United States Patent
Hijiya et al.

(10) Patent No.: US 7,205,433 B2
(45) Date of Patent: Apr. 17, 2007

(54) CRYSTAL OF AMINO ACID ESTER SALT AND PROCESS FOR PRODUCING THE SAME

(75) Inventors: Toyoto Hijiya, Yokkaichi (JP); Eriko Ono, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 226 days.

(21) Appl. No.: 11/062,879

(22) Filed: Feb. 23, 2005

(65) Prior Publication Data

US 2005/0197396 A1 Sep. 8, 2005

Related U.S. Application Data

(63) Continuation of application No. PCT/JP03/010623, filed on Aug. 22, 2003.

(30) Foreign Application Priority Data

Aug. 23, 2002 (JP) ............... 2002-243823

(51) Int. Cl.
*C07C 229/00* (2006.01)
(52) U.S. Cl. .................................... 562/553
(58) Field of Classification Search ................ None
See application file for complete search history.

(56) References Cited

FOREIGN PATENT DOCUMENTS

| JP | 42-22923 | 11/1967 |
| JP | 48-57915 | 8/1973 |
| JP | 55-151536 | 11/1980 |
| JP | 63-132866 | 6/1988 |

OTHER PUBLICATIONS

*Nippon Kagaku Kaishi*, vol. 83, 1962, pp. 1151-1154.
David J. Collins et al, *Aust. J. Chem.*, "Dihydro-1,2,4-triazin-6(1*H*)-ones. II* Synthesis of Several Methylated 3-Phenyl-4,5-dihydro-1,2,4-triazin-6(1*H*)-ones", vol. 52, 1999, pp. 379-385.
Tetsuo Kato; "Synthesis of Amino Acid Ethyl Ester p-Toluenesulfonate", *Nippon Kagaku Kaishi*, vol. 83, 1962, pp. 1151-1154 (with attached English translation).

*Primary Examiner*—Paul A. Zucker
(74) *Attorney, Agent, or Firm*—Oblon, Spivak, McClelland, Maier & Neustadt, P.C.

(57) ABSTRACT

The present invention provides a novel crystal of alanine alkyl ester sulfonate having low hygroscopicity and low corrosiveness, which can be produced industrially economically. The present invention provides crystals of alanine alkyl ester sulfonates represented by formula (1):

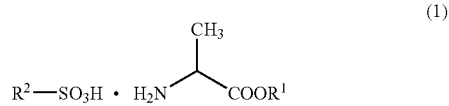

wherein $R^1$ is a methyl group or an ethyl group, provided that when $R^1$ is a methyl group, $R^2$ is an ethylphenyl group or a dimethylphenyl group; and when $R^1$ is an ethyl group, $R^2$ is a methyl group, a phenyl group, a chlorophenyl group, an ethylphenyl group, or a dimethylphenyl group.

20 Claims, 15 Drawing Sheets

CRYSTAL OF AMINO ACID ESTER SALT AND PROCESS FOR PRODUCING THE SAME

CROSS REFERENCES TO RELATED APPLICATIONS

This application is a continuation of International Patent Application No. PCT/JP03/010623, filed on Aug. 22, 2003, and claims priority to Japanese Patent Application No. 2002-243823, filed on Aug. 23, 2002, both of which are incorporated herein by reference in their entireties.

BACKGROUND OF THE INVENTION

1. Field of the Invention

The present invention relates to crystals of alanine alkyl ester sulfonates, which exhibit low hygroscopicity and low corrosiveness, and which are useful as intermediates for the production of pharmaceutical compounds having an alanine skeleton or as an alanine-containing peptide synthetic reagent. The present invention also relates to methods of producing such a crystal of an alanine alkyl ester sulfonate.

2. Discussion of the Background

Alanine lower alkyl ester compounds are useful as intermediates for the production of pharmaceutical compounds having an alanine skeleton or as alanine-containing peptide synthetic reagents. Generally, alanine lower alkyl esters are distributed in the form of a hydrochloride salt, and, for example, alanine methyl ester hydrochloride (hereinafter sometimes to be abbreviated as "Ala-OMe HCl salt"), alanine ethyl ester hydrochloride (hereinafter sometimes to be abbreviated as "Ala-OEt HCl salt"), and the like are commercially available. However, these hydrochlorides are hygroscopic and highly deliquescent, which makes handling thereof difficult. In addition, due to moisture absorption and deliquescence, the ester moiety such as alanine methyl ester (hereinafter sometimes to be abbreviated as "Ala-OMe"), alanine ethyl ester (hereinafter sometimes to be abbreviated as "Ala-OEt") and the like is hydrolyzed into methanol, ethanol and the like, and the purity becomes low. Particularly, when a synthetic reaction is carried out using such a compound, the alanine resulting from the decomposition reacts to produce a substance other than the desired product. Therefore, an extremely serious problem occurs when such compounds are used as starting materials for a pharmaceutical product required to have high purity.

As a substance other than hydrochloride, alanine ethyl ester hydrobromide, alanine ethyl ester p-toluenesulfonate (4-methylbenzenesulfonate) and the like are known. However, hydrohalides such as hydrochloride, hydrobromide, and the like exhibit a high corrosiveness to metals, and an industrial process using such a compound requires the use of equipment having a high resistance to corrosion.

In the case of p-toluenesulfonate, Kato et al. (*Nippon Kagaku Kaishi*, vol. 83, p. 1151 (1962)) obtained various amino acid ethyl ester p-toluenesulfonates as crystals by a method comprising an azeotropic dehydration treatment of p-toluenesulfonic acid and various amino acids in ethanol in the presence of carbon tetrachloride to effect esterification. However, Kato et al. reported that alanine ethyl ester p-toluenesulfonate became oily and failed to crystallize. On the other hand, DJ. Collins et al. (*Aust. J. Chem.*, 1999, vol. 52, pp. 379–385) reported that they obtained a crystal of alanine ethyl ester p-toluenesulfonate by transesterification using ethyl p-toluenesulfonate. However, when the present inventors tried to obtain L-alanine ethyl ester p-toluenesulfonate by transesterification, the reaction took a considerably long time and this method was found to be not entirely sufficient as an industrial production method.

Thus, there remains a need for crystals of alanine lower alkyl esters salts. There also remains a need for crystals of alanine lower alkyl esters salts, which exhibit reduced hygroscopicity. There also remains a need for crystals of alanine lower alkyl esters salts, which exhibit reduced corrosiveness. There also remains a need for a method for conveniently preparing such crystals.

SUMMARY OF THE INVENTION

Accordingly, it is one object of the present invention to provide novel crystals of alanine lower alkyl esters salts.

It is another object of the present invention to provide novel crystals of alanine lower alkyl esters salts, which exhibit reduced hygroscopicity.

It is another object of the present invention to provide novel crystals of alanine lower alkyl esters salts, which exhibit reduced corrosiveness.

It is another object of the present invention to provide novel crystals of alanine lower alkyl ester salts which exhibit reduced hygroscopicity (deliquescence) and low corrosiveness.

It is another object of the present invention to provide novel crystals of alanine lower alkyl esters salts, which can be produced efficiently on an industrial scale.

It is another object of the present invention to provide novel methods for the production of such crystals.

These and other objects, which will become apparent during the following detailed description, have been achieved by the inventors' discovery that a crystal of a particular sulfonic acid salt has markedly reduced hygroscopicity and corrosiveness as compared to Ala-OEt HCl salt and Ala-OMe HCl salt. Furthermore, they have found that this substance can be industrially produced easily.

Accordingly, the present invention provides the following:

(1) A crystal of alanine alkyl ester sulfonate, which is represented by formula (1):

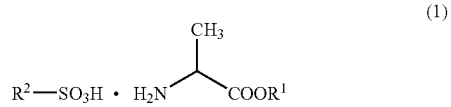

wherein $R^1$ is a methyl group or an ethyl group, provided that when $R^1$ is a methyl group, $R^2$ is an ethylphenyl group or a dimethylphenyl group; and when $R^1$ is an ethyl group, $R^2$ is a methyl group, a phenyl group, a chlorophenyl group, an ethylphenyl group, or a dimethylphenyl group.

(2) The crystal of the aforementioned (1), wherein, when $R^1$ is a methyl group, $R^2$ is a 4-ethylphenyl group, a 2,4-dimethylphenyl group, or a 2,5-dimethylphenyl group; and when $R^1$ is an ethyl group, $R^2$ is a methyl group, a phenyl group, a 4-chlorophenyl group, a 4-ethylphenyl group, a 2,4-dimethylphenyl group, or a 2,5-dimethylphenyl group.

(3) The crystal of the aforementioned (1), wherein $R^1$ is an ethyl group.

(4) The crystal of the aforementioned (1), wherein $R^1$ is a methyl group.

(5) The crystal of the aforementioned (1)–(4), wherein the alanine alkyl ester is an L form.

(6) A crystal of alanine alkyl ester methanesulfonate.

(7) A crystal of L or D-alanine alkyl ester methanesulfonate.

(8) A crystal of L-alanine ethyl ester methanesulfonate.

(9) A crystal of L-alanine ethyl ester benzenesulfonate.

(10) A crystal of L-alanine ethyl ester 4-chlorobenzenesulfonate.

(11) A crystal of L-alanine ethyl ester 4-ethylbenzenesulfonate.

(12) A crystal of L-alanine ethyl ester 2,4-dimethylbenzenesulfonate.

(13) A crystal of L-alanine ethyl ester 2,5-dimethylbenzenesulfonate.

(14) A crystal of L-alanine methyl ester 4-ethylbenzenesulfonate.

(15) A crystal of L-alanine methyl ester 2,4-dimethylbenzenesulfonate.

(16) A crystal of L-alanine methyl ester 2,5-dimethylbenzenesulfonate.

(17) A method of preparing a crystal of alanine alkyl ester sulfonate represented by formula (1):

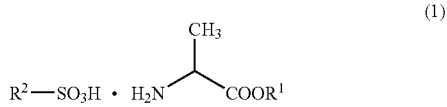

(1)

wherein $R^1$ is a methyl group or an ethyl group, provided that when $R^1$ is a methyl group, $R^2$ is an ethylphenyl group or a dimethylphenyl group; and when $R^1$ is an ethyl group, $R^2$ is a methyl group, a phenyl group, a chlorophenyl group, an ethylphenyl group, or a dimethylphenyl group, wherein the method comprises:

(a) contacting an alanine alkyl ester represented by formula (2):

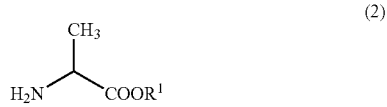

(2)

wherein $R^1$ is a methyl group or an ethyl group, with a sulfonic acid, to obtain an alanine alkyl ester sulfonate; and (b) crystallizing the alanine alkyl ester sulfonate.

(18) The method of the aforementioned (17), wherein, when $R^1$ is a methyl group, $R^2$ is a 4-ethylphenyl group, a 2,4-dimethylphenyl group, or a 2,5-dimethylphenyl group; and when $R^1$ is an ethyl group, $R^2$ is a methyl group, a phenyl group, a 4-chlorophenyl group, a 4-ethylphenyl group, a 2,4-dimethylphenyl group, or a 2,5-dimethylphenyl group.

(19) The method of the aforementioned (17), wherein $R^1$ is an ethyl group and $R^2$ is a methyl group.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
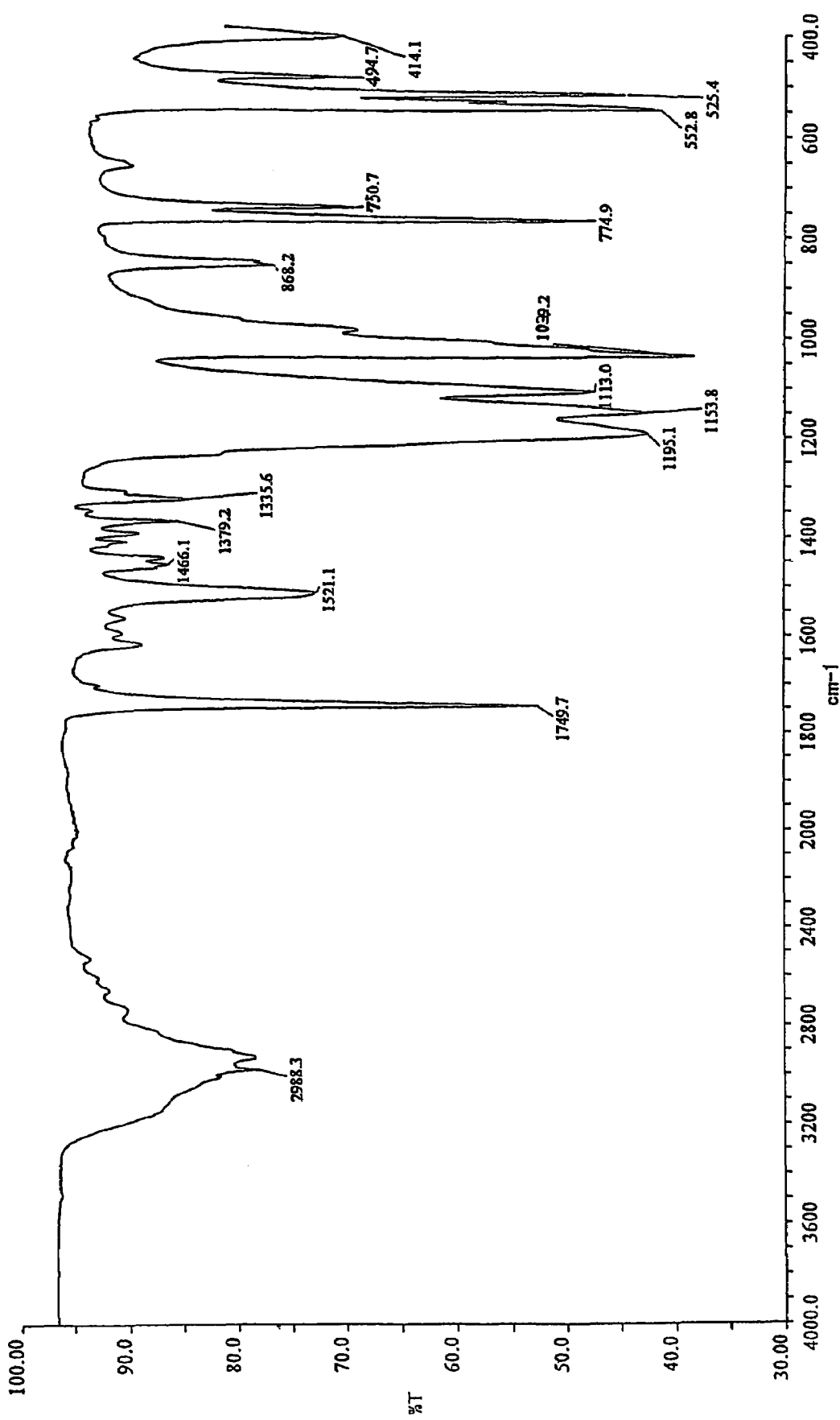
FIG. 1 is a chart of the infrared (IR) spectrum of the L-alanine ethyl ester methanesulfonate (hereinafter sometimes to be abbreviated as "L-Ala-OEt MsOH salt") obtained in Example 1.

The present invention is explained in detail in the following.

Alanine, alanine methyl ester, alanine ethyl ester, and alanine alkyl ester sulfonates such as alanine ethyl ester methanesulfonate and the like in this specification encompass a D form, an L form, racemic mixutes, racemates, and mixtures which exhibit enantiomeric enrichment between 0% and 100%, unless otherwise specified. By "L form," it is meant that the asymmetric carbon atom in the salt has the same configuration as in L-alanine, regardless of the actual direction of rotation of polarized light by the salt. Similarly, by "D form," it is meant that the asymmetric carbon atom in the salt has the same configuration as in D-alanine, regardless of the actual direction of rotation of polarized light by the salt.

Preferred examples of the crystal of alanine alkyl ester sulfonate represented by formula (I) include the following compounds:

crystal of alanine ethyl ester methanesulfonate, crystal of alanine ethyl ester benzenesulfonate, crystal of alanine ethyl ester 4-chlorobenzenesulfonate,
crystal of alanine ethyl ester 4-ethylbenzenesulfonate,
crystal of alanine ethyl ester 2,4-dimethylbenzenesulfonate,
crystal of alanine ethyl ester 2,5-dimethylbenzenesulfonate,
crystal of alanine methyl ester 4-ethylbenzenesulfonate,
crystal of alanine methyl ester 2,4-dimethylbenzenesulfonate, and
crystal of alanine methyl ester 2,5-dimethylbenzenesulfonate.

As for the the alanine alkyl ester sulfonate of the present invention, the L form is particularly preferable.

The alanine alkyl ester sulfonate of the present invention can be easily obtained by methods generally used for producing amino acid ester. In the following, alanine ethyl ester methanesulfonate is taken as an example for the explanation of the specific production method. However, the method is not limited to those shown below. Moreover, other alanine alkyl ester sulfonates of the present invention can be easily produced by similar methods, or a method analogous thereto.

Production Method 1. Method of esterifying alanine in ethanol in the presence of methanesulfonic acid.

This esterification is generally conducted at a reaction temperature of 15 to 80° C. for a reaction time of 30 minutes to 24 hours. For sufficient progress of the esterification reaction, the reaction solution is heated to about 90° C., and the reaction may be further carried out by adding ethanol while distilling away the same amount of ethanol.

Production Method 2. Method of obtaining the object methanesulfonate by contacting salt of volatile acid of alanine ethyl ester with methanesulfonic acid and removing liberated volatile acid to effect salt exchange.

As used herein, as the volatile acid, hydrochloric acid, hydrogen bromide, hydrogen fluoride, and the like can be mentioned, with preference given to hydrochloric acid and hydrogen bromide.

The reaction for contacting a salt of volatile acid of alanine ethyl ester with methanesulfonic acid is generally carried out at a reaction temperature of 0 to 80° C. for a reaction time of 1 minute to 24 hours.

As a method of removing the liberated volatile acid, evaporation, concentration under reduced pressure, and the like can be mentioned.

Production Method 3. Method of forming methanesulfonate by esterification of alanine in ethanol in the presence of an acid catalyst, adding methanesulfonic acid to the reaction mixture, and evaporating the existent volatile substance.

As the acid catalyst to be used for the esterification, hydrogen chloride gas, thionyl chloride, hydrogen bromide gas, thionyl bromide, and the like can be mentioned, and the esterification is generally carried out at a reaction temperature of 0 to 80° C. for a reaction time of 30 minutes to 24 hours.

As a method of evaporating a volatile substance, evaporation, concentration under reduced pressure, and the like can be mentioned.

Production Method 4. Method of forming methanesulfonate by esterification of alanine N-carboxyanhydride in ethanol containing methanesulfonic acid.

The esterification is generally carried out at a reaction temperature of !50 to 80° C. for a reaction time of 1 minute to 3 hours.

Production Method 5. Method of forming methanesulfonate by neutralization-extraction of alanine ethyl ester hydrochloride or hydrobromide in water containing an organic solvent immiscible with water and a basic substance, and adding methanesulfonic acid to the organic layer containing the alanine ethyl ester.

As the organic solvent immiscible with water to be used for this method, acetic acid esters such as ethyl acetate, isopropyl acetate, and the like; aromatic hydrocarbons such as toluene, xylene, and the like; hydrocarbons such as hexane, heptane, and the like; ethers such as diethyl ether, methyl tert-butyl ether, and the like, and halogenated hydrocarbons such as methylene chloride, chloroform, and the like, and the like can be mentioned.

As the basic substance, sodium hydrogencarbonate, sodium carbonate, sodium hydroxide, potassium hydroxide, ammonia, triethylamine, and the like can be mentioned.

As used herein, the neutralization-extraction means neutralizing a hydrochloric acid or hydrogen bromide moiety of alanine ethyl ester hydrochloride or hydrobromide with a basic substance, while extracting the liberated alanine ethyl ester with the organic solvent Production Method 6. Method of forming methanesulfonate by esterifying alanine in ethanol in the presence of mineral acid, neutralizing—extracting the reaction mixture with water containing an organic solvent immiscible with water and a basic substance, and adding methanesulfonic acid to the organic layer containing the alanine ethyl ester.

As used herein, as the mineral acid, hydrochloric acid, sulfuric acid, oxalic acid, phosphoric acid, and the like can be mentioned, and the esterification is generally carried out at a reaction temperature of 15 to 80° C. for a reaction time of 30 minutes to 24 hours. The organic solvent immiscible with water and the basic substance are the same as those in Production Method 5.

Of these Production Methods, Production Method 4 is difficult to handle, because alanine N-carboxyanhydride is unstable to heat, moisture, and the like, as well as expensive; and Production Methods 5 and 6 are hardly considered to be industrial production methods, because the extraction rate of alanine ethyl ester (or alanine methyl ester) with an organic solvent is not very high and the yield is low. In contrast, Production Methods 1, 2 and 3, wherein alanine alkyl ester is contacted with sulfonic acid, are industrially suitable and preferable production methods, because they use comparatively economical starting materials alone and afford high yields.

Since alanine alkyl ester sulfonates such as Ala-OEt MsOH salt and the like obtained by the aforementioned method show comparatively high solubility in a highly polar solvent such as water, alcohol and the like, they are not easily crystallized. They are not crystallized even by the methods of Production Methods 5 and 6, because the extracted organic layer contains water or alcohol, and they tend to become oily substances. To obtain crystals, therefore, crystallization is desirably performed by substitution of a solvent to one that decreases the solubility of Ala-OEt MsOH salt, or removing water contained therein by distillation and the like.

As a solvent that lowers the solubility, acetic acid esters such as ethyl acetate, isopropyl acetate, butyl acetate, and the like; aromatic hydrocarbons such as toluene, xylene, and the like; hydrocarbons such as hexane, heptane, and the like; and the like are used. Of these, acetic acid esters having the effect of suppressing the hydrolysis of Ala-OEt (or Ala-OMe) by competitive hydrolysis caused by moisture in the air are preferable. Particularly preferred is ethyl acetate (or methyl acetate) free of transesterification.

As a crystallization method, the following methods can be mentioned, but the method is not limited to those shown below.

Crystallization Method 1. Method of crystallization by adding a poor solvent to a solution wherein the alanine ethyl ester sulfonate, such as Ala-OEt MsOH salt and the like, has been formed (e.g., applied to Production Methods 1, 2, 3, and 4).

As the poor solvent to be used for this method, hydrocarbons such as hexane, heptane, and the like; aromatic hydrocarbons such as toluene, xylene, and the like; acetic acid esters such as ethyl acetate, isopropyl acetate, and the like; ethers such as diethyl ether, methyl tert-butyl ether, and the like; and the like can be mentioned.

Crystallization Method 2. Method of crystallization by concentrating or cooling a solution wherein the alanine ethyl ester sulfonic, acid salt such as Ala-OEt MsOH salt and the like, has been formed, thus affording a concentration of not less than the solubility (e.g., applied to Production Methods 5 and 6).

Crystallization Method 3. Method of crystallization by adding sulfonic acid such as methanesulfonic acid and the like to a state wherein Ala-OEt (or Ala-OMe) is dissolved in an organic solvent (e.g., applied to Production Methods 5 and 6).

For crystallization, a seed crystal may be added. The compound obtained by crystallization is separated by sedimentation, filtration, centrifugal separation, or the like, and washed, and dried, as necessary. Crystallization may be performed by adding the aforementioned solvent such as water, alcohol, and the like and a poor solvent as appropriate to the residue obtained by evaporating a solvent from a solution, wherein a salt has been formed, and drying to give a slurry, and then cooling the slurry without sufficiently dissolving the solid therein, and the like. In this case, however, the purity tends to become low. Therefore, it is preferable to perform crystallization after sufficiently dissolving the residue.

The hygroscopicity (deliquescence) of the crystals of alanine alkyl ester sulfonates of the present invention thus obtained was evaluated. As a result, the hygroscopicity was substantially absent under low humidity conditions, hygroscopicity was low even under high humidity conditions as compared to that of Ala-OEt HCl salt and Ala-OMe HCl salt, and no practical problem was found. In regard to corrosiveness, Ala-OEt HCl salt and Ala-OMe HCl salt showed corrosiveness against stainless, but the crystals of the alanine alkyl ester sulfonates of the present invention did not show corrosiveness.

Other features of the invention will become apparent in the course of the following descriptions of Examples, Comparative Examples, and Experimental Examples, which are given for illustration of the invention and are not intended to be limiting thereof.

EXAMPLES

The measurement equipment and conditions are shown in the following.

NMR: BRUKER AVANCE 400 (400MHz) melting point: BUCHI 535 (Examples 1–5), precision micromelting point measurement apparatus, Ishiishouten Co., Ltd. (Examples 6–13)

HPLC: (Examples 1–5)
column: Inertsil ODS-2 4.6 mm$\phi$×150 mm
detection wavelength: 210 nm
column temperature: 40° C.
injection volume: 20 μl
flow: 1.0 ml/min
mobile phase:
SOLUTION A 0.05M potassium dihydrogen phosphate (pH 2.0)
0.01M aqueous sodium octanesulfonate solution
SOLUTION B methanol
gradient conditions: 0 min A/B=82/18→15 min A/B=60/40

HPLC: (Examples 6–13)
column: Inertsil ODS-3 4.6 mm$\phi$×250 mm
detection wavelength: 210 nm
column temperature: 40° C.
injection volume: 50 μl
flow: 1.5 ml/min
mobile phase: {0.1M potassium dihydrogen phosphate (pH 2.3)+0.005M
sodium octanesulfonate}/acetonitrile=90/10

IR: Perkin Elmer Spectrum One
Measurement method ATR method (total reflection measurement method)

XRD (X ray diffraction): PHILIPS X-ray generator PW1710 (Examples 1–5), PHILIPS X-ray generator PW3050 (Examples 6–13)

MS: Electrospray ionization mass spectrometer TSQ700, Thermoquest

Example 1

Methanesulfonic acid (5.72 g, 59.52 mmol) was added to a slurry obtained by adding L-alanine (4.46 g, 50.06 mmol) to ethanol (25 ml) and dissolved therein. This solution was heated overnight at 70° C. to allow esterification. To complete the esterification reaction, triethyl orthoacetate (11 ml, 60 mmol) was added, and the mixture was stirred at 70° C. for 8 hours. Thereafter, the solvent was evaporated under reduced pressure, and ethyl acetate (15.96 g) was added to the obtained concentrated solid residue (12.14 g) to give a slurry. This slurry was filtered by suction, and the crystals were washed with ethyl acetate (3 ml). The obtained crystals (wet weight 12.33 g) were dried in vacuo to give dry crystals (10.01 g, 46.0 mmol).

As a result of HPLC analysis using L-Ala-OEt HCl salt as a standard product, the L-Ala-OEt MsOH salt content was 97.9 wt % (yield 91.9%).

$^1$H-NMR (400MHz, DMSO-d$_6$): 1.24 (3H, O—CH$_2$—CH$_3$, t, J=7.1Hz), 1.39 (3H, CH—CH$_3$, d, J=7.2Hz), 2.32 (3H, CH$_3$—SO$_3$, s), 4.09 (1H, N—CH—CO, q, J=7.2Hz), 4.21 (2H, O—CH$_2$—CH$_3$, q, J=7.1Hz), 8.28 (3H, NH$_3$, bs)

mp: 119° C.
IR: 1750cm$^{-1}$(ester C=O)
XRD (2θ, CuKα rays): 7.4°, 11.2°, 12.9°, 15.3°, 18.2°, 21.3°, 22.1°, 24.0°, 28.0°, 29.7°
ESI-MS: 118 (MH+; Ala-OEt), 191 ([2M–H]–; MsOH)

Figure 2:
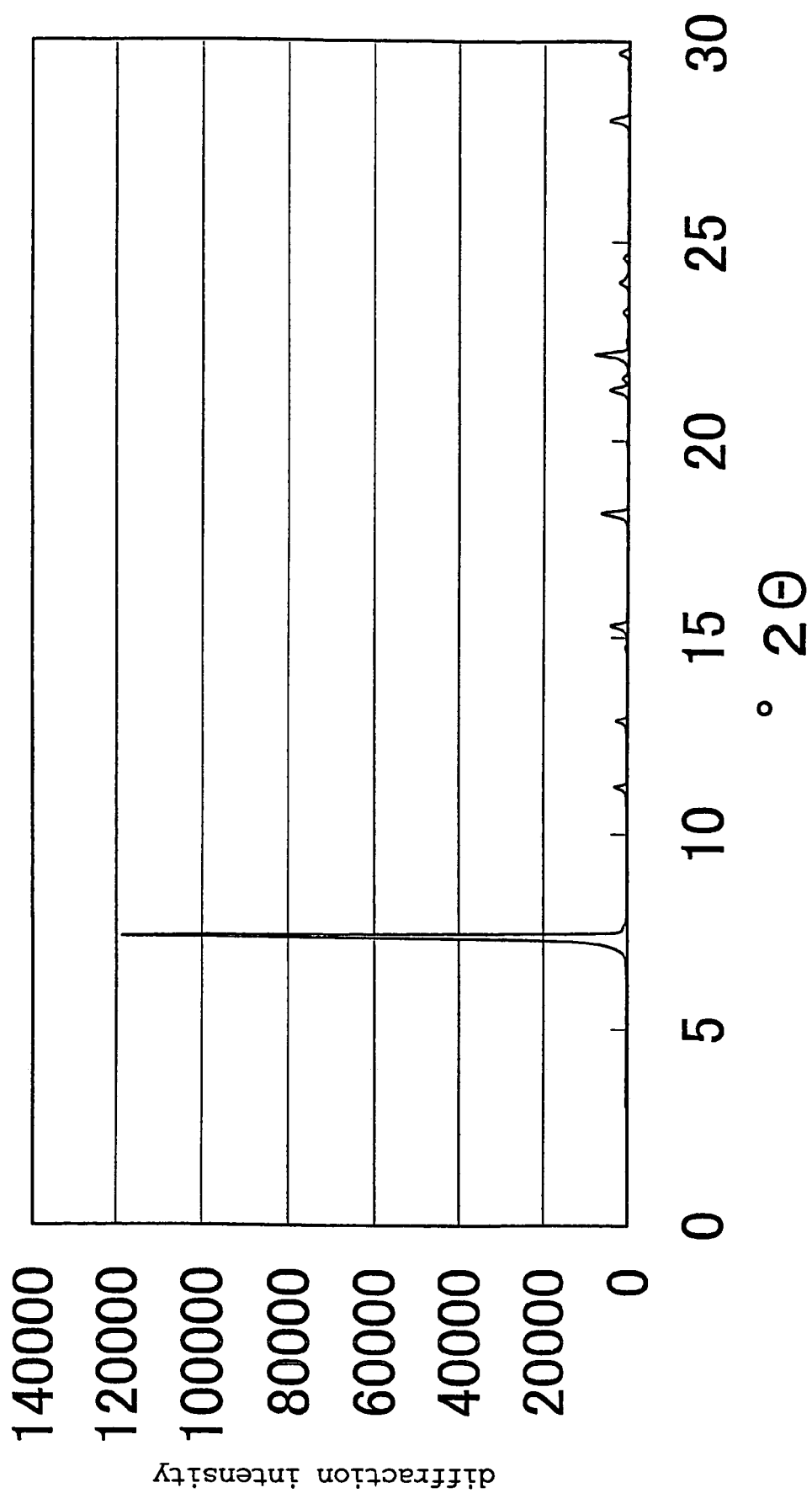
FIG. 2 is a powder X-ray diffraction pattern of the L-Ala-OEt MsOH salt obtained in Example 1.

The results of IR and XRD are shown in FIG. 1 and FIG. 2.

Example 2

L-Ala-OEt HCl salt (161.6 g, 1.053 mol) was suspended in ethyl acetate (400 ml), and methanesulfonic acid (69 ml, 1.063 mol) was added to allow dissolution. The solution was concentrated under reduced pressure to give a concentrate (278 g). Thereto was added ethyl acetate (200 ml), and the mixture was concentrated under reduced pressure to allow crystallization. Ethyl acetate (200 ml) was added to the obtained slurry (350 g), and the mixture was concentrated again under reduced pressure. Ethyl acetate (200 ml) was added to the obtained slurry (325 g), and the mixture was stirred at 8° C. for 5.5 hours. This slurry was filtered by suction, and the obtained wet crystals (225 g) were dried in vacuo to give L-Ala-OEt MsOH salt dry crystals (179 g, 0.839 mmol). yield 79.8% (L-Ala-OEt MsOH salt content 99.9%, yield 79.7%).

Example 3

Ethanol (302 L) was maintained at not higher than 15° C., and thionyl chloride (87 kg) was added over 4 hours. L-alanine (54.6 kg) was added, and the mixture was heated at 50° C. for 2 hours to allow esterification. A portion (10 ml, containing L-Ala-OEt HCl salt (2.559 g, 16.67 mmol) was taken from the obtained reaction mixture (370 L), and methanesulfonic acid (1.1 ml, 16.95 mmol) was added. The obtained solution was concentrated under reduced pressure. Ethyl acetate (30 ml) was added to the oily residue, and the mixture was concentrated again under reduced pressure. The oil concentrate (5.174 g) was dissolved in ethyl acetate (30 ml), and a small amount of L-Ala-OEt MsOH salt crystals was added to allow crystallization. The resulting crystals were preserved overnight in a refrigerator, collected by suction filtration, and washed with ethyl acetate (10 ml). The obtained wet crystals (3.566 g) were dried in vacuo to give L-Ala-OEt MsOH salt dry crystals (2.681 g, 12.58 mmol). yield 75.5% (L-Ala-OEt MsOH salt content 99.4%, 12.51 mmol, 75.0%).

Example 4

Methanesulfonic acid (0.795 ml, 12.25 mmol) was added to ethanol (50 ml), and L-alanine-N-carboxyanhydride (1.41 g, 12.25 mmol) was added with stirring. This reaction mixture was concentrated under reduced pressure, ethyl acetate (20 ml) was added to the obtained oil concentrate (2.785 g), and a small amount of L-Ala-OEt MsOH salt was added as a seed crystal to allow crystallization. The crystals were preserved in a refrigerator for 3 days, collected by suction filtration, washed with ethyl acetate (10 ml), and dried in vacuo to give L-Ala-OEt MsOH salt dry crystals (1.959 g, 9.19 mmol). yield 75.0%.

Example 5

L-Ala-OEt HCl salt (2.054 g, 13.38 mmol) was suspended in ethyl acetate (100 ml), and aqueous 6M NaOH solution (2.5 ml) and water (5 ml) were added. The mixture was stirred and extracted. The obtained ethyl acetate layer (88.3 g) was concentrated to 43.2 g under reduced pressure. Methanesulfonic acid (0.87 ml, 13.41 mmol) was added to allow crystallization. The crystals were preserved overnight in a refrigerator, collected by suction filtration, and washed with ethyl acetate (15 ml). The obtained wet crystals (1.995 g) were dried in vacuo to give L-Ala-OEt MsOH salt dry crystals (1.695 g, 7.95 mmol). yield 59.4% (L-Ala-OEt MsOH salt content 83.4%, 6.63 mmol, yield 49.6%).

Example 6

L-alanine (1.50 g, 16.84 mmol) and benzenesulfonic acid monohydrate (BsOH H$_2$0) (3.56 g, 20.20 mmol) were added to ethanol (10 ml), and the mixture was heated overnight at 70° C. to perform esterification. To complete the esterification reaction, the mixture was heated to 90° C. and ethanol (200 ml) was added over 3.5 hours while distilling away almost the same amount of ethanol. Thereafter, the solvent was evaporated under reduced pressure, and the residue was dried under reduced pressure. Ethanol (0.5 ml) and diethyl ether (30 ml) were added to partially crystallize an oily residue, and the mixture was stirred at room temperature to give a slurry. This slurry was cooled overnight in a refrigerator, and the crystals were separated and dried to give 4.55 g of L-alanine ethyl ester benzenesulfonate (L-Ala-OEt BsOH salt) dry crystals (L-Ala-OEt BsOH salt content 87.6%, (14.47 mmol), yield 86.0%).

$^1$H-NMR (400MHz, CD$_3$OD): 1.29 (3H, O—CH$_2$—C$\underline{H}_3$, t, J=7.2Hz), 1.51 (3H, CH—C$\underline{H}_3$, d, J=7.3Hz), 4.06 (1H, N—C$\underline{H}$—CO, q, J=7.3Hz), 4.26 (2H, O—C$\underline{H}_2$—CH$_3$, q, J=7.2Hz), 4.89 (N$\underline{H}_3$, bs), 7.39–7.45 (3H, benzene, m), 7.81–7.84 (2H, benzene, m)

ESI-MS: 118 (MH+; Ala-OEt), 159 (MH+; BsOH), 157 (MH−; BsOH)

mp: 92° C.

XRD (2θ, CuKα rays): 6.2°, 7.3°, 8.0°, 13.4°, 23.8°, 25.0°

Figure 3:
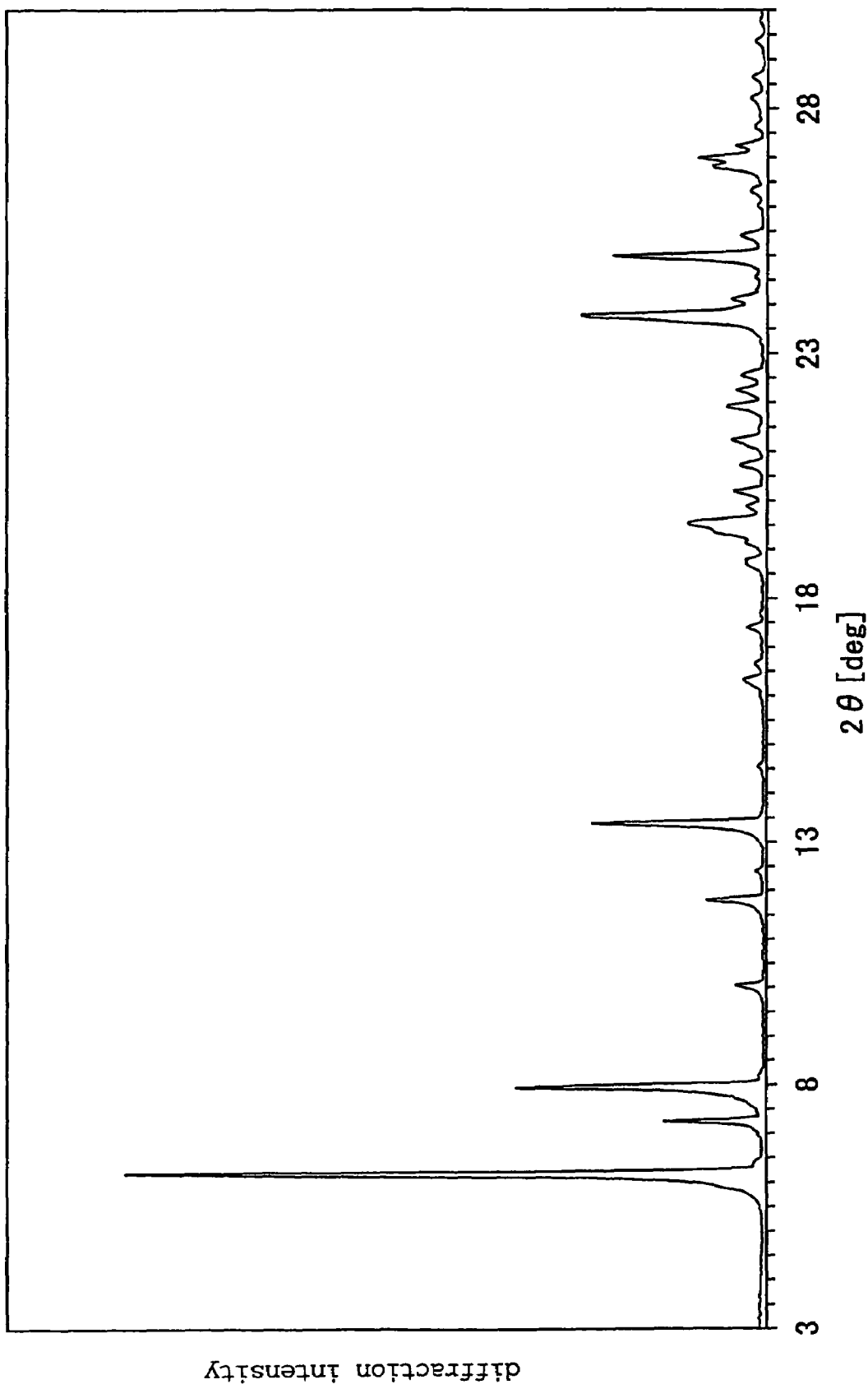
FIG. 3 is a powder X-ray diffraction pattern of the L-alanine ethyl ester benzenesulfonate (hereinafter sometimes to be abbreviated as "L-Ala-OEt BsOH salt") obtained in Example 6.

The results of XRD are shown in FIG. 3.

Example 7

L-alanine (1.50 g, 16.84 mmol) and 4-chlorobenzenesulfonic acid (4-CBS) (3.89 g, 20.20 mmol) were added to ethanol (15 ml), and the mixture was heated overnight at 70 EC to perform esterification. To complete the esterification reaction, the mixture was heated to 90 EC, and ethanol (200 ml) was added over 3.5 hours, while distilling away almost the same amount of ethanol. Thereafter, the solvent was evaporated under reduced pressure, and the residue was dried under reduced pressure. Ethanol (1 ml) and diethyl ether (60 ml) were added to partially crystallize an oily residue and the mixture was stirred at room temperature to give a slurry. This slurry was cooled overnight in a refrigerator and the crystals were separated and dried to give 3.52 g of L-alanine ethyl ester 4-chlorobenzenesulfonate (L-Ala-OEt 4-CBS salt) dry crystals (L-Ala-OEt 4-CBS salt content 93.6%, 10.64 mmol, yield 63.2%).

$^1$H-NMR (400MHz, CD$_3$OD): 1.29 (3H, O—CH$_2$—C$\underline{H}_3$, t, J=7.2Hz), 1.52 (3H, CH—C$\underline{H}_3$, d, J=7.3Hz), 4.08 (1H, N—C$\underline{H}$—CO, q, J=7.3Hz), 4.26 (2H, O—C$\underline{H}_2$—CH$_3$, q, J=7.2Hz), 4.91 (N$\underline{H}_3$, bs), 7.42–7.45 (2H, benzene, m), 7.78–7.81 (2H, benzene, m)

ESI-MS: 118 (MH+; Ala-OEt), 191 (MH−; 4-CBS)

mp: 133° C.

XRD (2θ, CuKα rays): 6.0°, 6.7°, 11.2°, 11.9°, 13.0°, 20.1°, 22.4°, 28.5°

Figure 4:
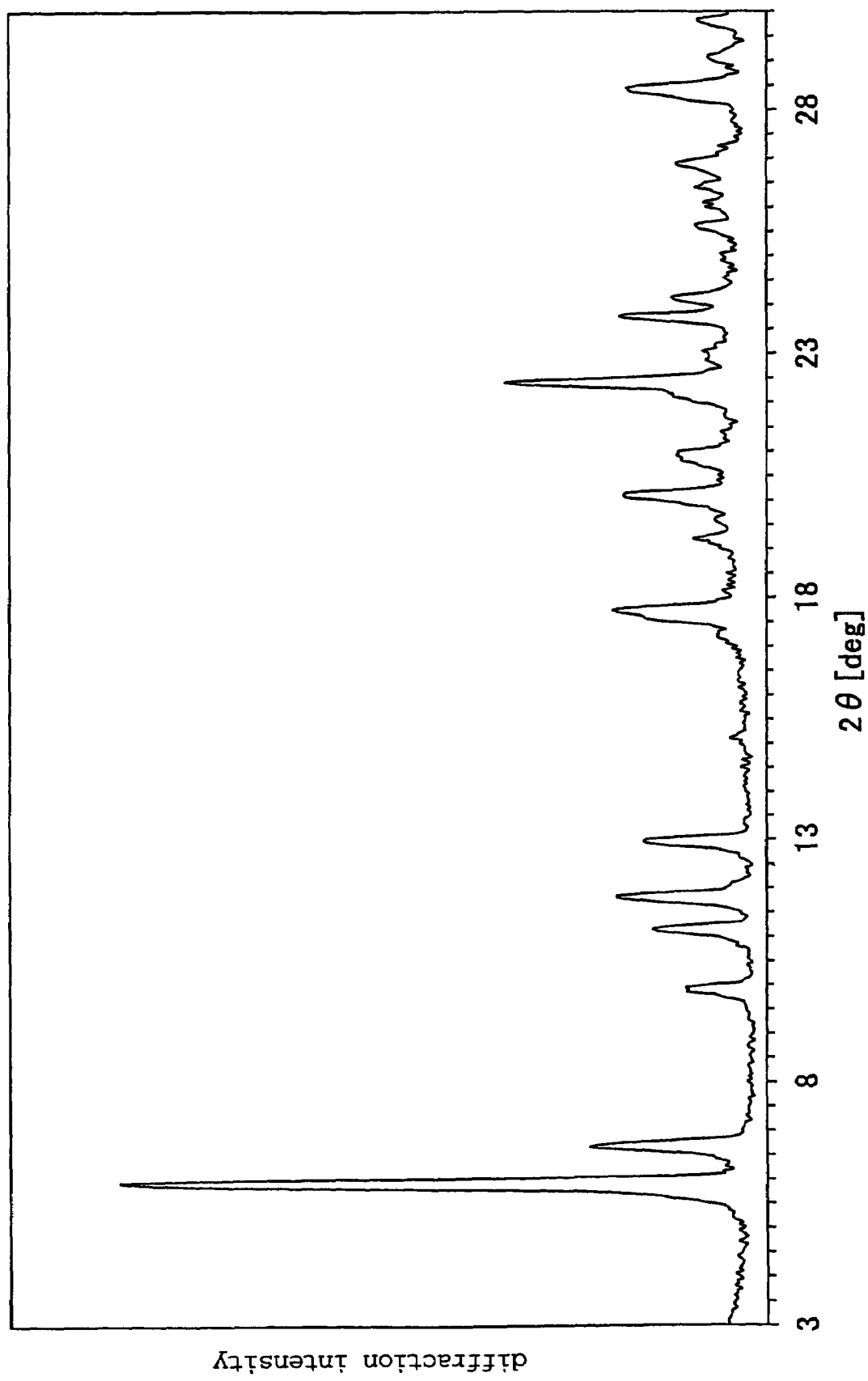
FIG. 4 is a powder X-ray diffraction pattern of the L-alanine ethyl ester 4-chlorobenzenesulfonate (hereinafter sometimes to be abbreviated as "L-Ala-OEt 4-CBS salt") obtained in Example 7.

The results of XRD are shown in FIG. 4.

Example 8

L-alanine (1.50 g, 16.84 mmol) and 4-ethylbenzenesulfonic acid (4-EBS) (3.76 g, 20.20 mmol) were added to ethanol (15 ml), and the mixture was heated overnight at 70 EC to perform esterification. To complete the esterification reaction, the mixture was heated to 90 EC, and ethanol (200 ml) was added over 3.5 hours, while distilling away almost the same amount of ethanol. Thereafter, the solvent was evaporated under reduced pressure, and the residue was dried under reduced pressure. The obtained oily residue was cooled in a refrigerator to allow partial crystallization. Diethyl ether (5 ml) and ethyl acetate (5 ml) were added, the residue was completely dissolved at 40° C., and the mixture was stirred at room temperature. Since crystallization occurred when a vessel containing the reaction solution was immersed in ice water, ethyl acetate (15 ml) was further added, and the mixture was stirred at room temperature to give a slurry. This slurry was cooled overnight in a refrigerator, and the crystals were separated and dried to give 2.98 g of L-alanine ethyl ester 4-ethylbenzenesulfonate (L-Ala-OEt 4-EBS salt) dry crystals (L-Ala-OEt 4-EBS salt content 98.5%, 9.67 mmol, yield 57.4%).

$^1$H-NMR (400MHz, CD$_3$OD): 1.23 (3H, CH$_2$—C$\underline{H}_3$, t, J=7.6Hz), 1.29 (3H, O—CH$_2$—C$\underline{H}_3$, t, J=7.2Hz), 1.51 (3H, CH—C$\underline{H}_3$, d, J=7.2Hz), 2.67 (2H, C$\underline{H}_2$—CH$_3$, q, J=7.6Hz), 4.06 (1H, N—C$\underline{H}$—CO, q, J=7.2Hz), 4.26 (2H, O—C$\underline{H}_2$—CH$_3$, q, J=7.2Hz), 4.84 (N$\underline{H}_3$, bs), 7.26 (2H, benzene, d, J=8.1Hz), 7.73 (2H, benzene, d, J=8.1Hz)

ESI-MS: 118 (MH+; Ala-OEt), 185 (MH−; 4-EBS)

mp: 85° C.

XRD (2θ, CuKα rays): 7.6°, 13.4°, 16.4°, 19.3°, 22.8°

Figure 5:
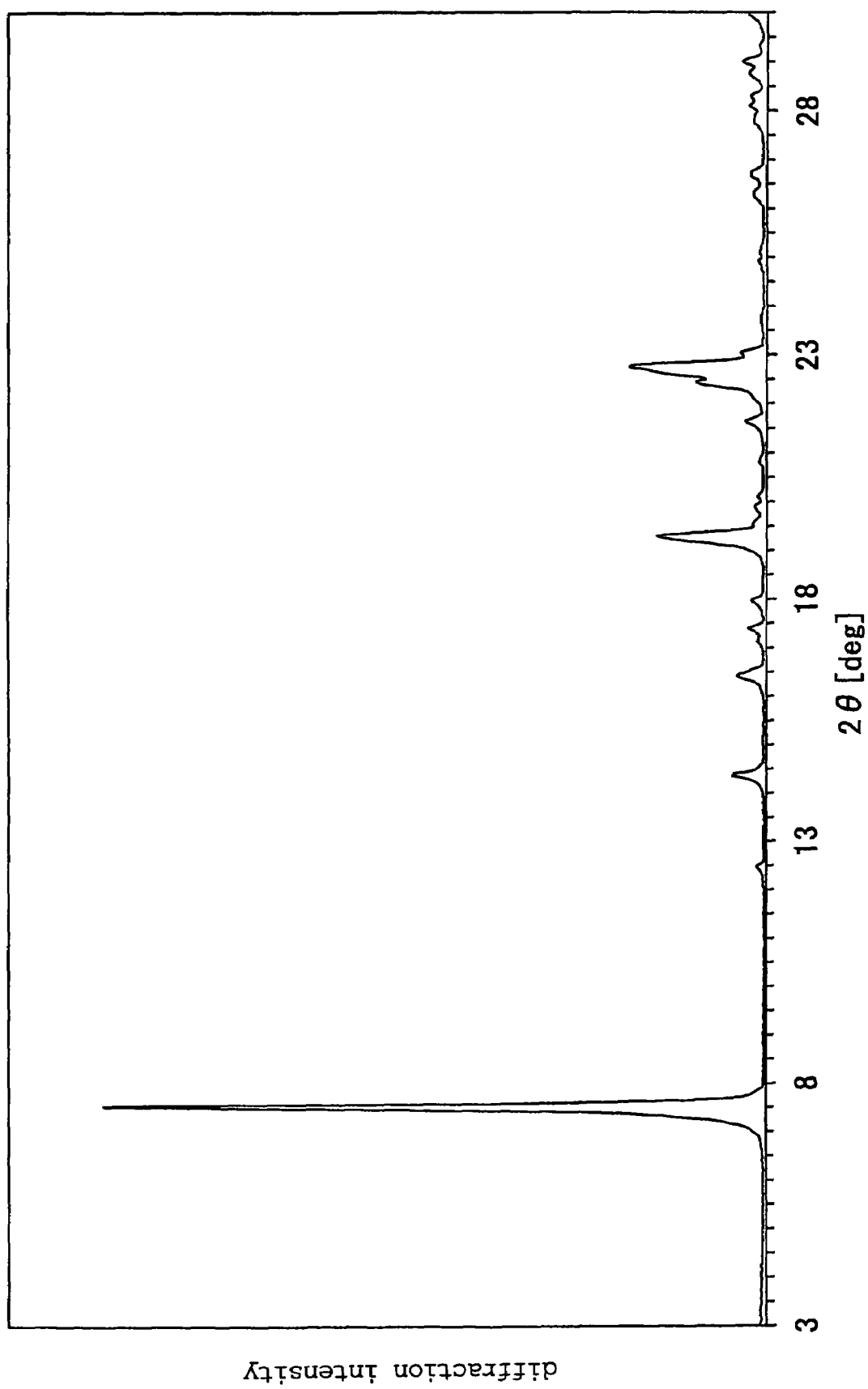
FIG. 5 is a powder X-ray diffraction pattern of the L-alanine ethyl ester 4-ethylbenzenesulfonate (hereinafter sometimes to be abbreviated as "L-Ala-OEt 4-EBS salt") obtained in Example 8.

The results of XRD are shown in FIG. 5.

Example 9

L-alanine (1.50 g, 16.84 mmol) and 2,4-dimethylbenzenesulfonic acid (2,4-DMBS) (3.76 g, 20.20 mmol) were added to ethanol (15 ml), and the mixture was heated overnight at 70 EC to perform esterification. To complete the esterification reaction, the mixture was heated to 90 EC, and ethanol (200 ml) was added over 3.5 hours, while distilling away almost the same amount of ethanol. Thereafter, the solvent was evaporated under reduced pressure, and the residue was dried under reduced pressure. The obtained oily residue was cooled in a refrigerator to allow partial crystallization. Diethyl ether (2.5 ml) and ethyl acetate (17.5 ml) were added, and the residue was dissolved almost entirely at 50° C. The mixture was stirred at room temperature to give a slurry. This slurry was cooled overnight in a refrigerator, and the crystals were separated and dried to give 3.00 g of L-alanine ethyl ester 2,4-dimethylbenzenesulfonate (L-Ala-OEt 2,4-DMBS salt) dry crystals (L-Ala-OEt 2,4-DMBS salt content 99.6%, 9.84 mmol, yield 58.4%).

$^1$H-NMR (400MHz, CD$_3$OD): 1.28 (3H, O—CH$_2$—C$\underline{H}_3$, t, J=7.2Hz), 1.51 (3H, CH—C$\underline{H}_3$, d, J=7.3Hz), 2.30 (3H, C$\underline{H}_3$, s), 2.61 (3H, C$\underline{H}_3$, s), 4.05 (1H, N—C$\underline{H}$—CO, q, J=7.3Hz), 4.25 (2H, O—C$\underline{H}_2$—CH$_3$, q, J=7.2Hz), 4.84 (N$\underline{H}_3$, bs), 7.00 (1H, benzene, d, J=8.0Hz), 7.06 (1H, benzene, s), 7.77 (1H, benzene, d, J=8.0Hz)

ESI-MS: 118 (MH+; Ala-OEt), 185 (MH−; 2,4-DMBS)

mp: 104° C.

XRD (2θ, CuKα rays): 7.4°, 10.5°, 14.7°, 19.1°, 22.2°, 24.2°

Figure 6:
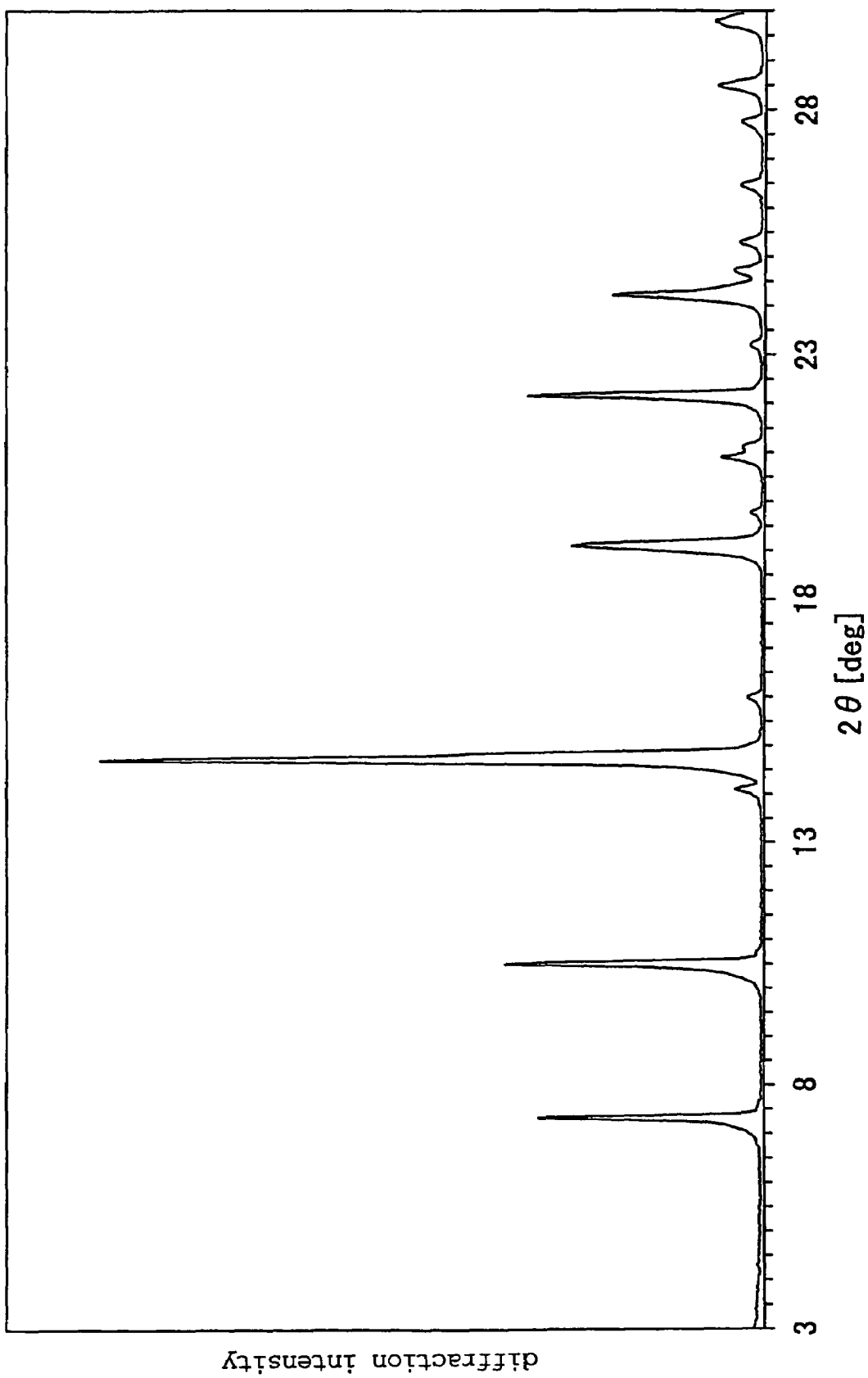
FIG. 6 is a powder X-ray diffraction pattern of the L-alanine ethyl ester 2,4-dimethylbenzenesulfonate (hereinafter sometimes to be abbreviated as "L-Ala-OEt 2,4-DMBS salt") obtained in Example 9.

The results of XRD are shown in FIG. 6.

Example 10

L-alanine (1.50 g, 16.84 mmol) and 2,5-dimethylbenzenesulfonic acid (2,5-DMBS) (3.76 g, 20.20 mmol) were added to ethanol (15 ml), and the mixture was heated overnight at 70° C. to perform esterification. To complete the esterification reaction, the mixture was heated to 90° C., and ethanol (200 ml) was added over 3.5 hours, while distilling away almost the same amount of ethanol. Thereafter, the solvent was evaporated under reduced pressure, and the residue was dried under reduced pressure. The obtained oily residue was cooled in a refrigerator to allow partial crystallization. Ethyl acetate (7 ml) was added, and the residue was dissolved almost entirely at 50° C. The mixture was stirred at room temperature, diethyl ether (40 ml) was further added, and the mixture was stirred at room temperature to give a slurry. The obtained slurry was cooled overnight in a refrigerator, and the crystals were separated and dried to give 3.77 g of L-alanine ethyl ester 2,5-dimethylbenzenesulfonate (L-Ala-OEt 2,5-DMBS salt) dry crystals (L-Ala-OEt 2,5-DMBS salt content 95.6%,11.88 mmol, yield 70.5%).

$^1$H-NMR (400MHz, CD$_3$OD): 1.29 (3H, O—CH$_2$—C$\underline{H}_3$, t, J=7.2Hz), 1.51 (3H, CH—C$\underline{H}_3$, d, J=7.2Hz), 2.31 (3H, C$\underline{H}_3$, s), 2.60 (3H, C$\underline{H}_3$, s), 4.06 (1H, N—C$\underline{H}$—CO, q, J=7.2Hz), 4.26 (2H, O—C$\underline{H}_2$—CH$_3$, q, J=7.2Hz), 4.84 (N$\underline{H}_3$, bs), 7.12 (2H, benzene, s), 7.74 (1H, benzene, s)

ESI-MS: 118 (MH+; Ala-OEt), 185 (MH−; 2,5-DMBS)

mp: 132° C.

XRD (2θ, CuKα rays): 7.6°, 12.8°, 15.1°, 16.8°, 17.8°, 18.4°, 19.7°, 22.7°

Figure 7:
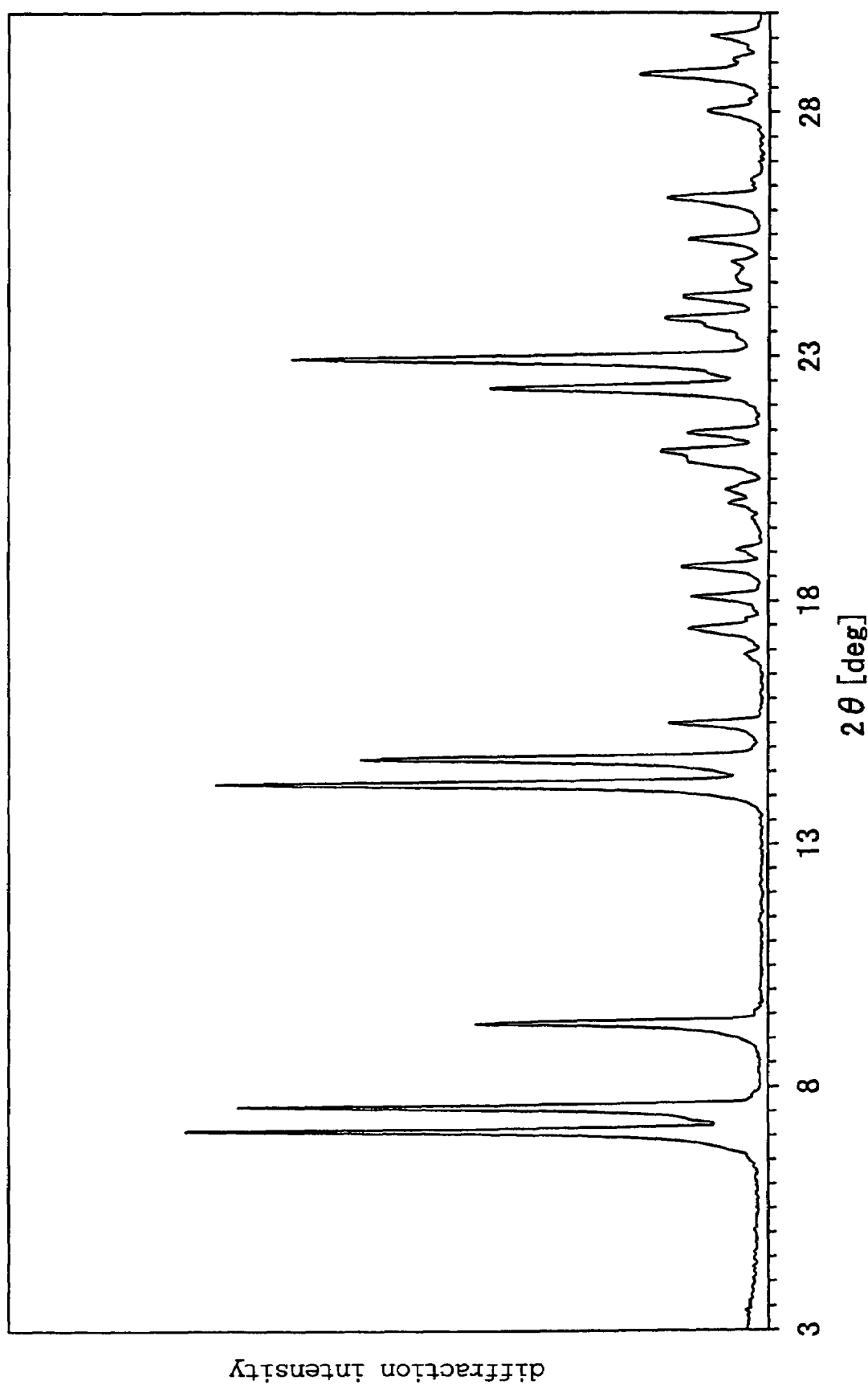
FIG. 7 is a powder X-ray diffraction pattern of the L-alanine ethyl ester 2,5-dimethylbenzenesulfonate (hereinafter sometimes to be abbreviated as "L-Ala-OEt 2,5-DMBS salt") obtained in Example 10.

The results of XRD are shown in FIG. 7.

Example 11

L-Ala-OMe HCl salt (1.00 g, 7.16 mmol) was suspended in methyl acetate (15 ml). 4-Ethylbenzenesulfonic acid (4-EBS) (1.60 g, 8.57 mmol) was added, and the mixture was stirred for dissolution. This solution was concentrated under reduced pressure, methyl acetate (15 ml) was added, and the mixture was concentrated twice under reduced pressure. The obtained concentrate was cooled in a refrigerator. Since partial crystallization occurred, methyl acetate (15 ml) was added to dissolve the crystals at 50° C. This solution was stirred at room temperature to give a slurry. This slurry was cooled overnight in a refrigerator and the crystals were separated and dried to give 1.04 g of L-alanine methyl ester 4-ethylbenzenesulfonate (L-Ala-OMe 4-EBS salt) dry crystals (L-Ala-OMe 4-EBS salt content 100%, 3.42 mmol, yield 47.8%).

$^1$H-NMR (400MHz, CD$_3$OD): 1.23 (3H, CH$_2$—C$\underline{H}_3$, t, J=7.6Hz), 1.51 (3H, CH—C$\underline{H}_3$, d, J=7.3Hz), 2.67 (2H, C$\underline{H}_2$—CH$_3$, q, J=7.6Hz), 3.81 (3H, O—C$\underline{H}_3$, s), 4.09 (1H, N—C$\underline{H}$—CO, q, J=7.3Hz), 4.84 (N$\underline{H}_3$, bs), 7.25–7.27 (2H, benzene, m), 7.71–7.74 (2H, benzene, m)

ESI-MS: 104 (MH+; Ala-OMe), 185 (MH−; 4-EBS)

mp: 105° C.

XRD (2θ, CuKα rays): 8.1°, 8.5°, 14.2°, 21.7°, 22.2°, 24.4°

Figure 8:
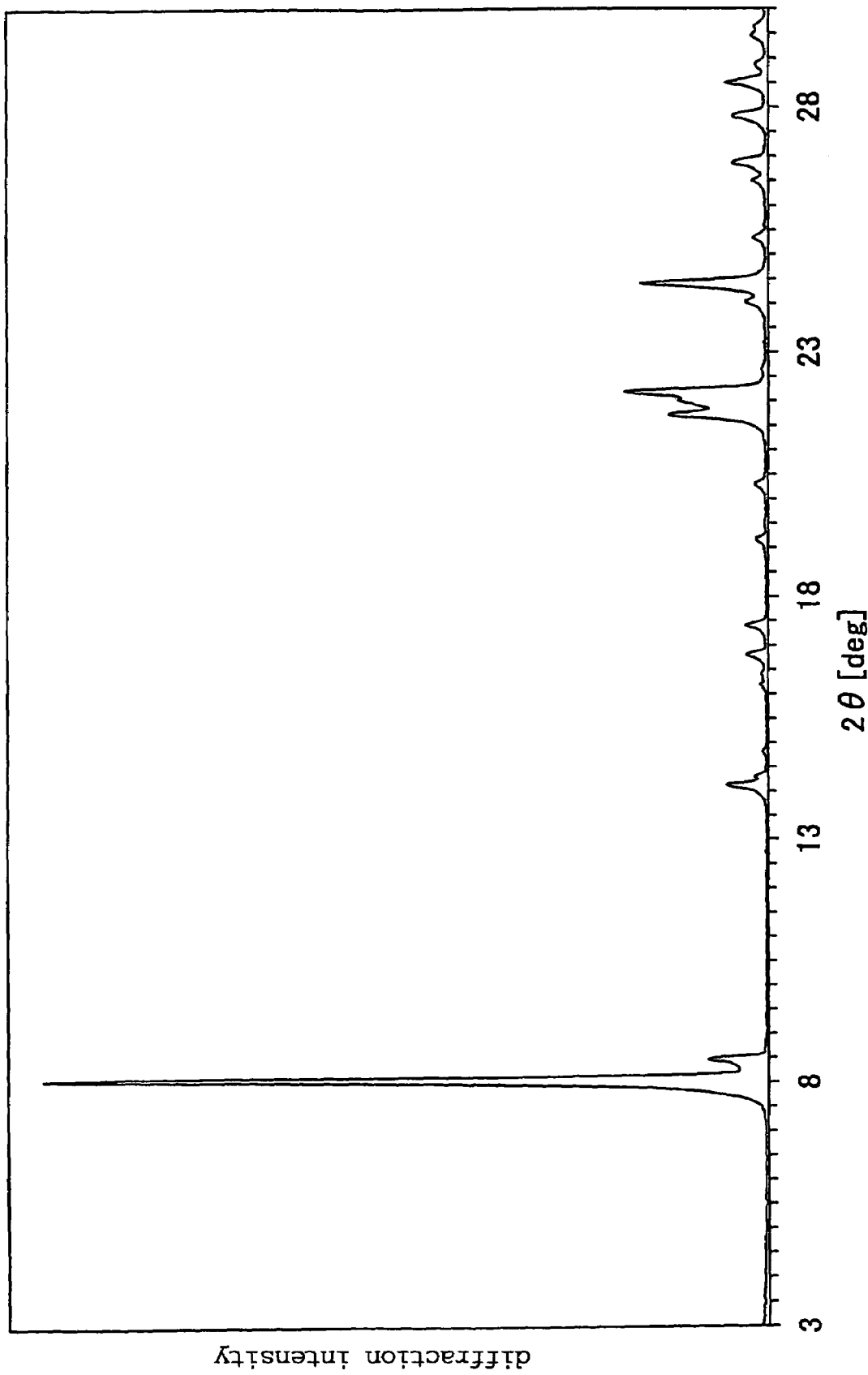
FIG. 8 is a powder X-ray diffraction pattern of the L-alanine methyl ester 4-ethylbenzenesulfonate (hereinafter sometimes to be abbreviated as "L-Ala-OMe 4-EBS salt") obtained in Example 11.

The results of XRD are shown in FIG. 8.

Example 12

L-Ala-OMe HCl salt (0.68 g, 4.87 mmol) was suspended in methyl acetate (15 ml). 2,4-Dimethylbenzenesulfonic acid (2,4-DMBS) (1.09 g, 5.85 mmol) was added, and the mixture was stirred for dissolution. This solution was concentrated under reduced pressure, methyl acetate (15 ml) was added, and the mixture was concentrated twice under reduced pressure. The obtained concentrate was cooled in a refrigerator. Since partial crystallization occurred, methyl acetate (5 ml) and diethyl ether (15 ml) were added to dissolve the crystals by stirring at room temperature. This solution was stirred under ice-cooling to give a slurry. This slurry was cooled overnight in a refrigerator, and the crystals were separated and dried to give 1.18 g of L-alanine methyl ester 2,4-dimethylbenzenesulfonate (L-Ala-OMe 2,4-DMBS salt) dry crystals (L-Ala-OMe 2,4-DMBS salt 92.9%, 4.11 mmol, yield 84.4%).

$^1$H-NMR (400MHz, CD$_3$OD): 1.51 (3H, CH—C$\underline{H}_3$, d, J=7.1Hz), 2.31 (3H, C$\underline{H}_3$, s), 2.61 (3H, C$\underline{H}_3$, s), 3.81 (3H, O—C$\underline{H}_3$, s), 4.09 (1H, N—C$\underline{H}$—CO, q, J=7.1Hz), 4.84 (N$\underline{H}_3$, bs), 7.00 (1H, benzene, d, J=8.0Hz), 7.06 (1H, benzene, s), 7.77 (1H, benzene, d, J=8.0Hz)

Figure 9:
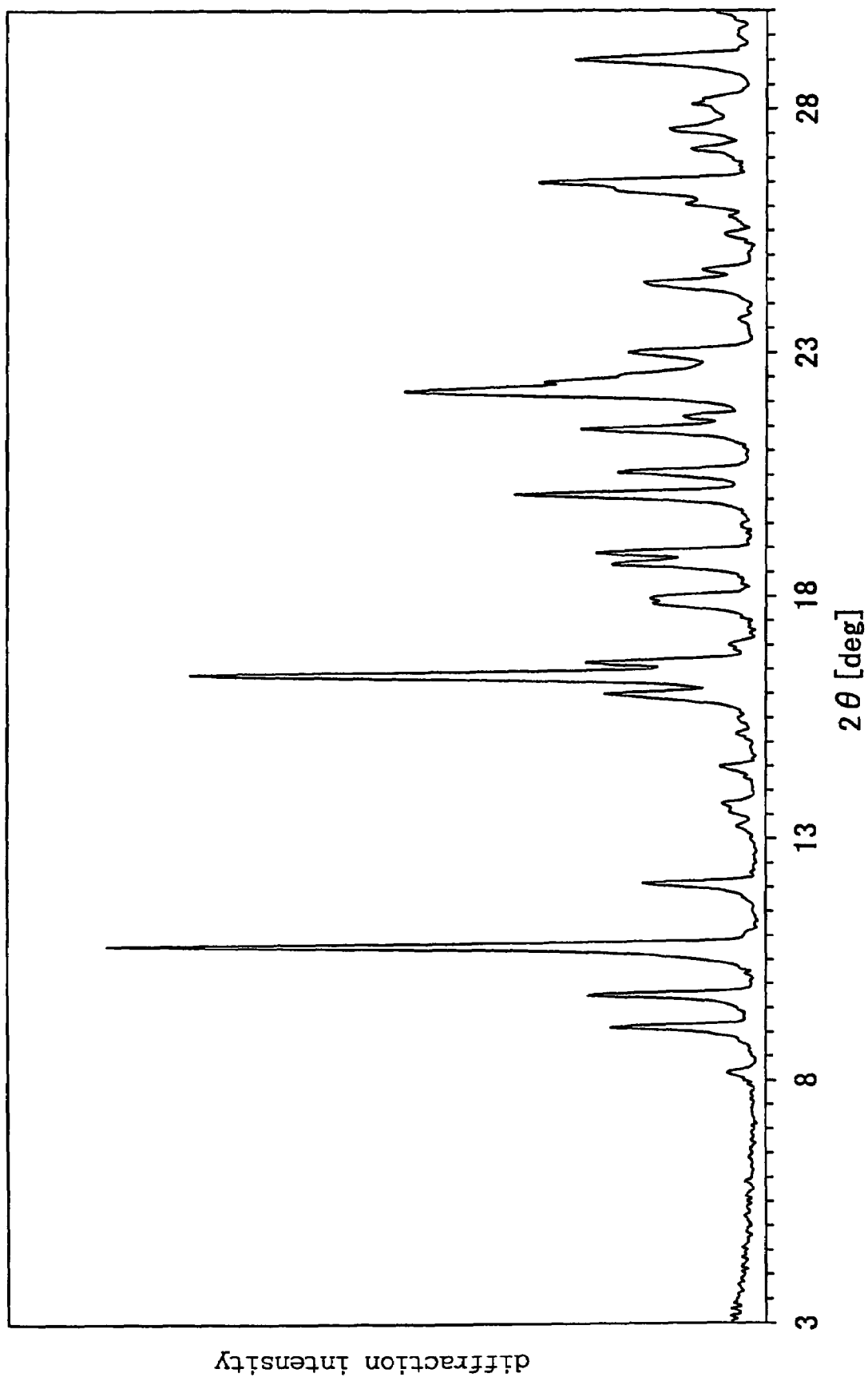
FIG. 9 is a powder X-ray diffraction pattern of the L-alanine methyl ester 2,4-dimethylbenzenesulfonate (hereinafter sometimes to be abbreviated as "L-Ala-OMe 2,4-DMBS salt") obtained in Example 12.

ESI-MS: 104 (MH+; Ala-OMe), 185(MH−; 2,4-DMBS)
mp: 78° C.
XRD (2θ, CuKα rays): 9.1°, 9.8°, 10.8°, 12.1°, 16.4°, 20.1°, 22.2°, 26.5°
The results of XRD are shown in FIG. 9.

Example 13

L-Ala-OMe HCl salt (1.00 g, 7.16 mmol) was suspended in methyl acetate (15 ml). 2,5-Dimethylbenzenesulfonic acid (2,5-DMBS) (1.60 g, 8.59 mmol) was added, and the mixture was stirred for dissolution. This solution was concentrated under reduced pressure, methyl acetate (15 ml) was added, and the mixture was concentrated twice under reduced pressure to allow crystallization. Methyl acetate (15 ml) was added to dissolve the obtained slurry almost entirely at 50° C. This solution was stirred at room temperature to give a slurry. This slurry was cooled overnight in a refrigerator, and the crystals were separated and dried to give 1.87 g of L-alanine methyl ester 2,5-dimethylbenzenesulfonate (L-Ala-OMe 2,5-DMBS salt) dry crystals (L-Ala-OMe 2,5-DMBS salt content 98.9%, 6.23 mmol, yield 87.0%).

Figure 10:
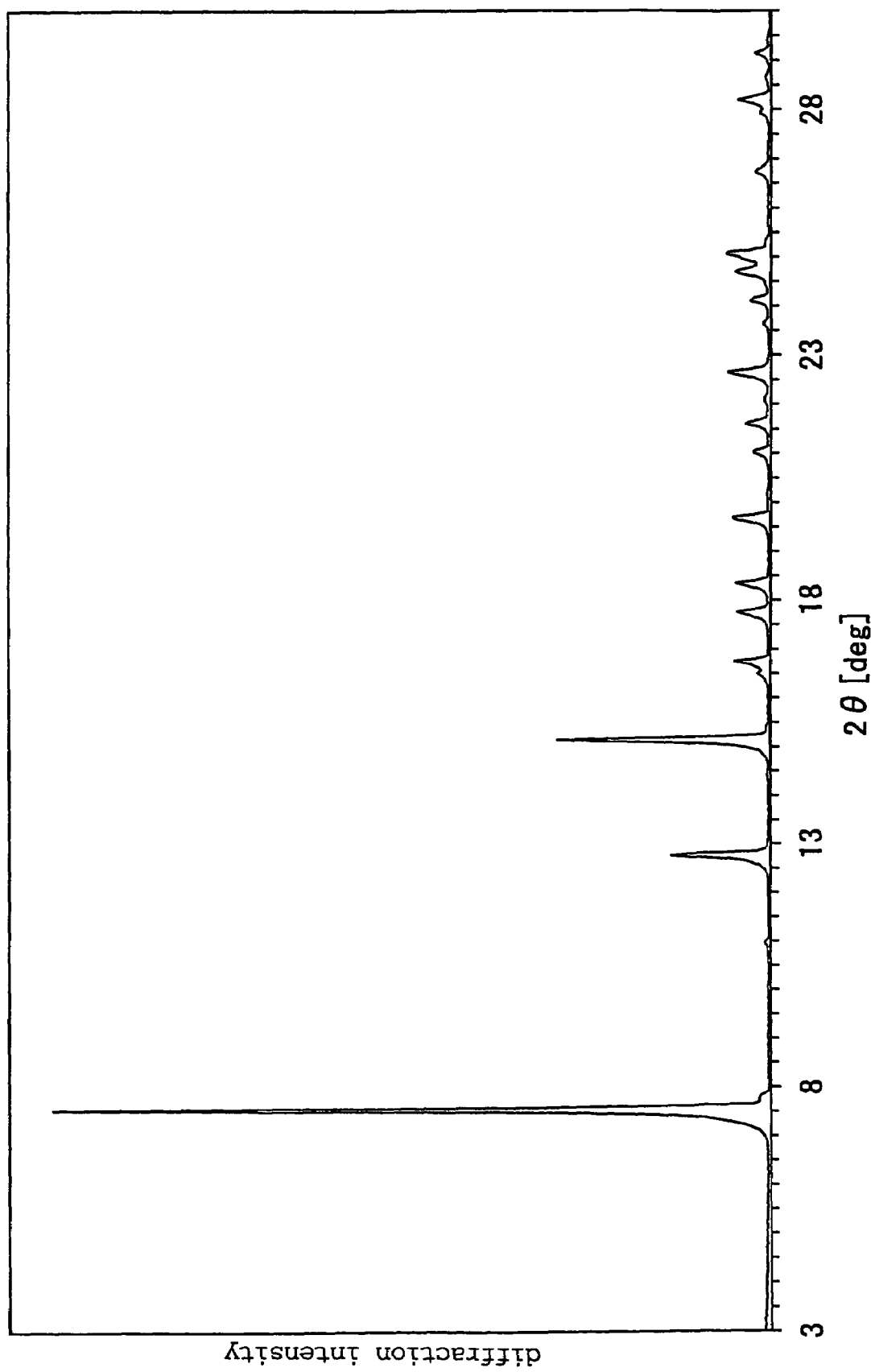
FIG. 10 is a powder X-ray diffraction pattern of the L-alanine methyl ester 2,5-dimethylbenzenesulfonate (hereinafter sometimes to be abbreviated as "L-Ala-OMe 2,5-DMBS salt") obtained in Example 13.

$^1$H-NMR (400MHz, CD$_3$OD): 1.51 (3H, CH—C$\underline{H}_3$, d, J=7.3Hz), 2.31 (3H, C$\underline{H}_3$, s), 2.60 (3H, C$\underline{H}_3$, s), 3.80 (3H, O—C$\underline{H}_3$, s), 4.09 (1H, N—C$\underline{H}$—CO, q, J=7.3Hz), 4.85 (N$\underline{H}_3$, bs), 7.13 (2H, benzene, s), 7.73 (1H, benzene, s)
ESI-MS: 104 (MH+; Ala-OMe), 185 (MH−; 2,5-DMBS)
mp: 165° C.
XRD (2θ, CuKα rays): 7.6°, 12.8°, 15.2°, 16.8°, 17.8°, 18.4°, 19.7°, 22.7° The results of XRD are shown in FIG. 10.

Comparative Examples 1–5

The same operation as in Examples 1–5 was performed except that methanol, methyl acetate, and L-Ala-OMe HCl salt were used instead of ethanol, ethyl acetate and L-Ala-OEt HCl salt, respectively, but L-alanine methyl ester methanesulfonate(L-Ala-OMe MsOH salt) was obtained only as an oily substance and did not crystallize.

Comparative Example 6

Acetyl bromide (4.75 ml, 64.2 mmol) was added dropwise to ethanol (30 ml) cooled to −5° C. to allow generation of hydrogen bromide. L-alanine (4.46 g, 50.06 mmol) was added to this solution, and the mixture was heated at 50° C. for 12 hours. Then, triethyl orthoacetate (10 ml, 54.6 mmol) was added and the mixture was heated at 70° C. for 7 hours to perform esterification. Thereafter, the mixture was concentrated under reduced pressure. Ethyl acetate (10 ml) was added to the obtained oily residue, and the mixture was concentrated again under reduced pressure. Ethyl acetate (20 ml) was added to the obtained oily residue (10.2 g), and the mixture was stored overnight in a refrigerator. However, the solution remained unchanged and crystallization did not occur.

Comparative Example 7

L-Ala-OEt HCl salt (1.04 g, 6.78 mmol) was suspended in ethyl acetate (10 ml), and triethyl orthoacetate (0.5 ml, 2.73 mmol) and 97% sulfuric acid (0.38 ml, 6.92 mmol) were added. The mixture was concentrated under reduced pressure. Ethyl acetate was added to the obtained oily residue, but the oily substance did not dissolve, and crystallization did not occur. Toluene and methyl tert-butyl ether were similarly added to the oily residue, but crystallization did not occur.

Comparative Example 8

L-alanine (2.29 g, 25.67 mmol) was added to methanol (5 ml), and methyl orthoformate (5 ml, 45.7 mmol) was added thereto. Methanesulfonic acid (2 ml, 30.82 mmol) was added, and the mixture was heated at 55° C. for 21 hours to perform esterification. A portion (1 ml) was taken from the obtained esterification reaction mixture (11.3 g) and concentrated under reduced pressure. Cyclohexane was added to the obtained oily residue, but crystallization did not occur. Similarly, a portion was taken from the esterification reaction mixture and concentrated under reduced pressure. Toluene, acetonitrile and methyl acetate were added to the residue, but crystallization did not occur.

Comparative Example 9

L-Ala-OMe HCl salt (1.00 g, 7.16 mmol) was suspended in methyl acetate (15 ml), and benzenesulfonic acid monohydrate (BsOH H$_2$O) (1.51 g, 8.57 mmol) was added. The mixture was stirred for dissolution. This solution was concentrated under reduced pressure, and methyl acetate (15 ml) was added. The mixture was concentrated twice under reduced pressure, and the obtained concentrate was cooled in a refrigerator. Since partial crystallization occurred, diethyl ether (3 ml) and methyl acetate (15 ml) were added to dissolve the crystals almost entirely at 40° C. This solution was stirred at room temperature and cooled overnight in a refrigerator. The crystals were separated and dried to give L-alanine methyl ester benzenesulfonate (L-Ala-OMe BsOH salt) crystals. The crystals were left standing at room temperature for a while. As a result, the crystals were liquefied and failed to provide stable crystals.

Comparative Example 10

L-alanine (1.50 g, 16.84 mmol) and 98% phosphoric acid (2.02 g, 20.20 mmol) were added to ethanol (10 ml), and the mixture was heated at 65° C. to perform esterification reaction. L-alanine was once dissolved, but crystals gradually precipitated. Therefore, the crystals were separated 8 hours later. The obtained crystals were L-alanine. The mother liquor was analyzed by HPLC and found to show almost no progress of the reaction.

Comparative Example 11

L-alanine (1.50 g, 16.84 mmol) and citric anhydride (3.88 g, 20.20 mmol) were added to ethanol (10 ml), and the mixture was heated at 65 EC to perform esterification reaction. L-alanine did not dissolve, but the mixture was stirred overnight as it was. The slurry was separated and confirmed to be L-alanine. The mother liquor was analyzed by HPLC and found to show almost no progress of the reaction.

Comparative Example 12

L-alanine (1.50 g, 16.84 mmol) and ethyl p-toluenesulfonate (ethyl 4-methylbenzenesulfonate (3.71 g, 18.52 mmol) were added to ethanol (10 ml), and the mixture was heated at 65 EC to perform esterification reaction. After 72 hr, the reaction was completed (reaction yield 90%), and the reaction mixture was concentrated under reduced pressure. Ethyl acetate (15 ml) was added to the obtained concentrate, and the mixture was stirred. The insoluble materials were removed by filtration, the mixture was concentrated again under reduced pressure, and ethyl acetate (15 ml) was added. Cooling in a refrigerator did not lead to crystallization.

Comparative Example 13

L-alanine (1.50 g, 16.84 mmol) and 4-methylbenzenesulfonic acid monohydrate (3.84 g, 20.20 mmol) were added to ethanol (15 ml), and the mixture was heated overnight at 70 EC to perform esterification reaction. To complete the esterification reaction, the mixture was heated to 90 EC, and ethanol (200 ml) was added over 3.5 hours, while distilling away almost the same amount of ethanol. Thereafter, the solvent was evaporated under reduced pressure, and the residue was dried under reduced pressure, and cooled in a refrigerator, but crystallization did not occur.

Comparative Example 14

L-alanine (1.50 g, 16.84 mmol) and 4-hydroxybenzenesulfonic acid (3.52 g, 20.20 mmol) were added to ethanol (15 ml), and the mixture was heated overnight at 70 EC to perform esterification reaction. To complete the esterification reaction, the mixture was heated to 90 EC, and ethanol (200 ml) was added over 3.5 hours, while distilling away almost the same amount of ethanol. Thereafter, the solvent was evaporated under reduced pressure, and the residue was dried under reduced pressure, and cooled in a refrigerator, but crystallization did not occur.

Comparative Example 15

L-alanine (1.50 g, 16.84 mmol) and methanesulfonic acid (1.94 g, 20.20 mmol) were added to ethanol (10 ml), and the mixture was heated at 65 EC for 5.5 hr to perform esterification reaction. Thereafter, the solvent was evaporated under reduced pressure, and methyl acetate (6 ml) was added to the obtained concentrate. The mixture became cloudy upon stirring. Cooling in a refrigerator did not result in crystallization.

Comparative Example 16

L-alanine (1.15 g, 12.91 mmol) and 4-methylbenzenesulfonic acid (2.66 g, 15.45 mmol) were added to methanol (18 ml), and the mixture was heated overnight at 65 EC to perform esterification reaction. Thereafter, the solvent was evaporated under reduced pressure, and methyl acetate (8 ml) was added to the obtained concentrate. The mixture was cooled in a refrigerator, but crystallization did not occur.

Comparative Example 17

L-alanine (1.00 g, 11.22 mmol) and benzenesulfonic acid (2.13 g, 13.47 mmol) were added to methanol (20 ml), and the mixture was heated overnight at 65 EC to perform esterification reaction. Thereafter, the solvent was evaporated under reduced pressure, and methyl acetate (10 ml) was added to the obtained concentrate. The mixture was stirred to give an oily substance. The obtained oily substance was cooled in a refrigerator, but crystallization did not occur.

Comparative Example 18

L-alanine (1.50 g, 16.84 mmol) and 4-hydroxybenzenesulfonic acid (3.52 g, 20.21 mmol) were added to methanol (20 ml), and the mixture was heated overnight at 65 EC to perform esterification reaction. Thereafter, the solvent was evaporated under reduced pressure, and methyl acetate (10 ml) was added to the obtained concentrate. The mixture was stirred to give an oily substance. Then, methanol (3 ml) was added to dissolve the oily substance. The solution was cooled in a refrigerator, but crystallization did not occur.

Experimental Example 1

Figure 11:
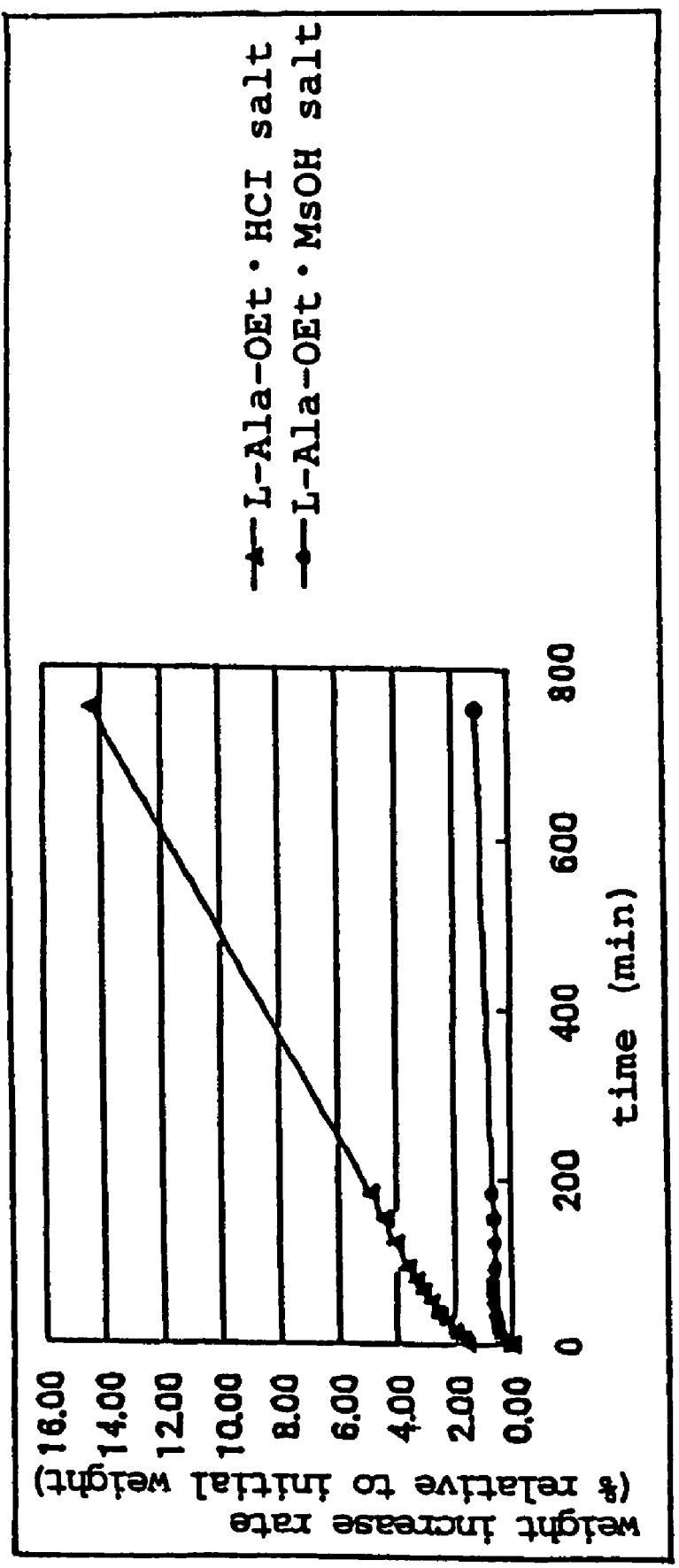
FIG. 11 is a graph of the results presented in Table 1.

Comparison of Hygroscopicity Between the L-Ala-OEt HCl Salt and the L-Ala-OEt MsOH Salt L-Ala-OEt HCl salt and L-Ala-OEt MsOH salt were measured into in a glass container in an amount of 1.6 g each, dried in vacuo at 30° C. for 5 hours, left under conditions of temperature: 22 to 24° C., humidity: 44 to 45% RH, and then the hygroscopicity was compared based on the weight gain over the lapse of time. The L-Ala-OEt HCl salt showed liquefaction of a part of the crystals in 60 minutes. The liquefied portion increased with the lapse of time, and the entire salt became liquid 750 minutes later with no observable crystal. In contrast, the L-Ala-OEt MsOH salt showed almost no change in weight with the lapse of time, and liquefaction was not observed. The results are shown in Table 1 and FIG. 11.

TABLE 1

Comparison of hygroscopicity between L-Ala-OEt HCl salt and L-Ala-OEt MsOH salt.

| Time (minutes) | weight increase rate (% relative to initial weight) | |
| --- | --- | --- |
| | L-Ala-OEt HCl salt | L-Ala-OEt MsOH salt |
| 0 | 0.00 | 0.00 |
| 1 | 1.63 | 0.08 |
| 2 | 1.67 | 0.11 |
| 3 | 1.72 | 0.17 |
| 4 | 1.73 | 0.17 |
| 6 | 1.80 | 0.23 |
| 10 | 1.95 | 0.36 |
| 15 | 2.07 | 0.41 |
| 25 | 2.29 | 0.48 |
| 35 | 2.55 | 0.56 |
| 50 | 2.88 | 0.58 |
| 60 | 3.09 (partly liquefied) | 0.59 |
| 75 | 3.38 | 0.63 |
| 90 | 3.63 | 0.57 |
| 120 | 4.10 | 0.58 |
| 150 | 4.41 | 0.58 |
| 180 | 4.89 | 0.61 |
| 750 | 14.37 (whole liquid) | 1.16 |

Experimental Example 2

Comparison of Hygroscopicity Between L-Ala-OEt MsOH Salt and L-Ala-OMe HCl Salt.

Figure 12:
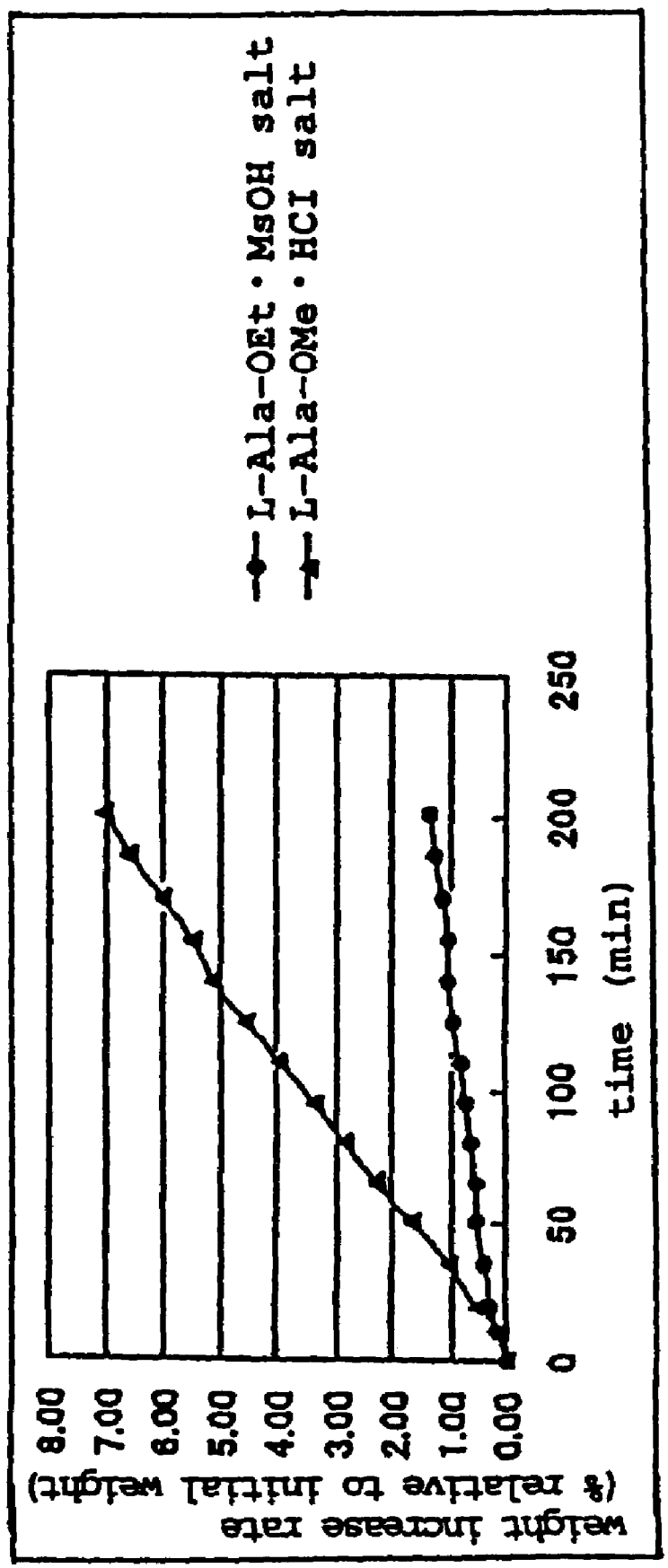
FIG. 12 is a graph of the results presented the values in Table 2.

In the same manner as in Experimental Example 1, L-Ala-OEt MsOH salt and L-Ala-OMe HCl salt were measured into a glass container in an amount of 0.6 g each, left under conditions of temperature: 24° C., humidity: 62 to 64% RH, and then the hygroscopicity was compared based on the weight gain with the lapse of time. The L-Ala-OMe HCl salt showed liquefaction of a part of the crystals in 20 minutes. The liquefied portion increased with the lapse of time and the entire salt became liquid 155 minutes later with no observable crystal. In contrast, the L-Ala-OEt MsOH salt showed not much change in weight with the lapse of time, and liquefaction was not observed. The results are shown in Table 2 and FIG. 12.

TABLE 2

Comparison of hygroscopicity between
L-Ala-OEt MsOH salt and L-Ala-OMe HCl salt.

| Time (minutes) | weight increase rate (% relative to initial weight) | |
| --- | --- | --- |
| | L-Ala-OEt MsOH salt | L-Ala-OMe HCl salt |
| 0 | 0.00 | 0.00 |
| 10 | 0.18 | 0.11 |
| 20 | 0.26 | 0.54 (partly liquefied) |
| 35 | 0.39 | 1.04 |
| 50 | 0.53 | 1.67 |
| 65 | 0.55 | 2.27 (whole sherbet) |
| 80 | 0.63 | 2.83 |
| 95 | 0.70 | 3.36 |
| 110 | 0.78 | 3.97 |
| 125 | 0.94 | 4.54 |
| 140 | 1.01 | 5.13 |
| 155 | 1.00 | 5.48 (whole liquid) |
| 170 | 1.13 | 6.02 |
| 185 | 1.26 | 6.56 |
| 200 | 1.32 | 7.03 |

Experimental Example 3

Ccomparison of Corrosiveness

A small amount of crystals of each of L-Ala-OEt HCl salt, L-Ala-OEt MsOH salt, and L-Ala-OMe HCl salt was placed on a stainless plate (SUS 316 L), stored under an atmosphere at 22° C., 30% RH, and the corrosion state of the stainless plate was observed. When one day passed, the L-Ala-OEt HCl salt and the L-Ala-OMe HCl salt caused a brown rust on the stainless plate, and at day 7, the rust increased. After the lapse of 7 days, the plate was moved to at atmosphere at 24° C., 65% RH. After 9 hours, the L-Ala-OEt HCl salt became a brown liquid with the color of the rust, and the L-Ala-OMe HCl salt became a colorless liquid. On the other hand, the L-Ala-OEt MsOH salt showed no change during this period, and no rust was found on the stainless plate. The results are show in Table 3.

TABLE 3

Comparison of corrosiveness of L-Ala-OEt HCl salt,
L-Ala-OEt MsOH salt and L-Ala-OMe HCl salt to stainless.

| No. of days | L-Ala-OEt HCl salt | L-Ala-OEt MsOH salt | L-Ala-OMe HCl salt |
| --- | --- | --- | --- |
| Day 1 | development of brown rust on a part of stainless plate | No change | development of brown rust on a part of stainless plate |
| Day 7 | enlarged brown rust on stainless plate | No change | enlarged brown rust on stainless plate (smaller than L-Ala-OEt HCl salt) |
| Day 8 (after standing at 24° C., 65% RH) | brown liquid | No change of crystal No change of stainless plate | colorless liquid |

Experimental Example 4

Comparison of Hygroscopicity

Figure 13:
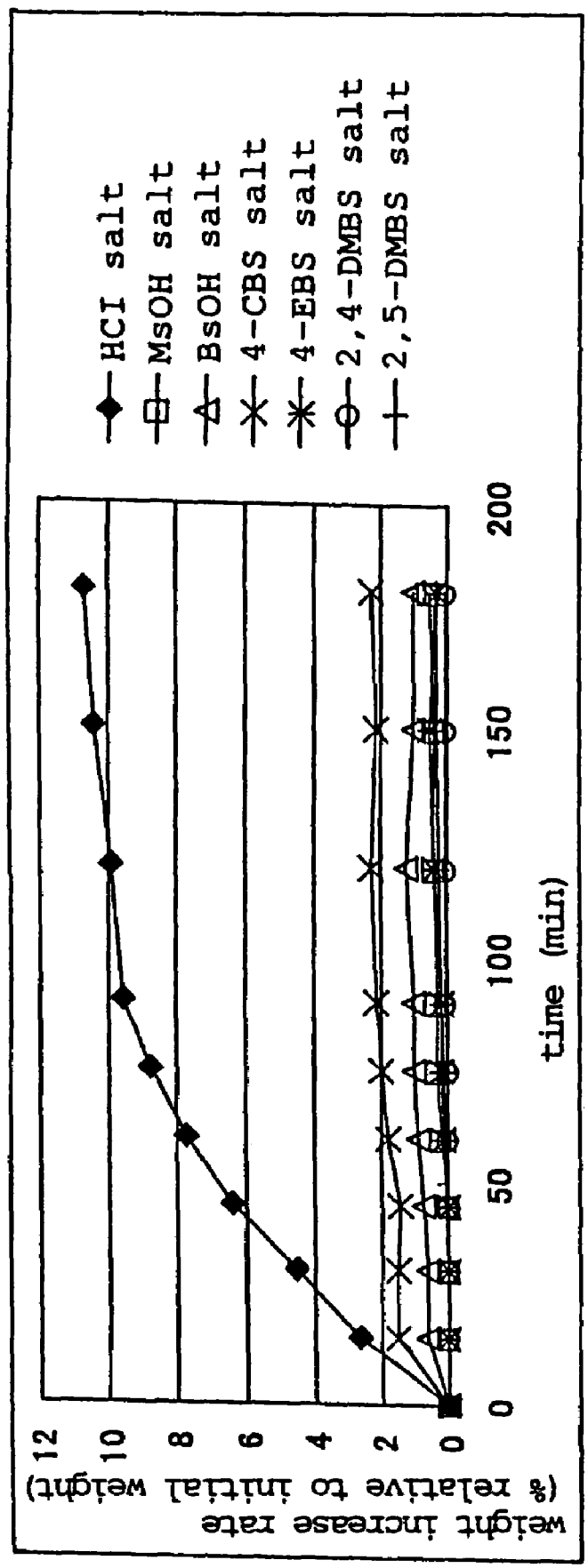
FIG. 13 is a graph of the results presented the values in Table 4.

The L-Ala-OEt HCl salt, L-Ala-OEt MsOH salt, L-Ala-OEt BsOH salt, L-Ala-OEt 4-CBS salt, L-Ala-OEt 4-EBS salt, L-Ala-OEt 2,4-DMBS salt, and L-Ala-OEt 2,5-DMBS salt were measured in an amount of about 0.3 g each, left standing in a thermostatic chamber at a temperature of 24° C. and a humidity of 40 to 46% RH, and the hygroscopicity was compared based on the weight gain with the lapse of time. A part of the crystal of the L-Ala-OEt HCl salt was liquefied in 30 minutes, and the liquefied portion increased thereafter with the lapse of time. After 100 minutes, the whole mass became like a sherbet. In contrast, the other salts showed almost no change in weight with the lapse of time, and liquefaction was not observed. The results are shown in Table 4 and FIG. 13.

TABLE 4

| Time (minutes) | weight increase rate (%) L-Ala-OEt | | | | | | |
| --- | --- | --- | --- | --- | --- | --- | --- |
| | HCl salt | MsOH salt | BsOH salt | 4-CBS salt | 4-EBS salt | 2,4-DMBS salt | 2,5-DMBS salt |
| 0 | 0.00 | 0.00 | 0.00 | 0.00 | 0.00 | 0.00 | 0.00 |
| 15 | 2.63 | 0.03 | 0.66 | 1.55 | 0.00 | 0.00 | 0.00 |
| 30 | 4.56 (partly liquefied) | 0.03 | 0.63 | 1.51 | 0.00 | 0.00 | 0.00 |

TABLE 4-continued

| | | | weight increase rate (%) L-Ala-OEt | | | | |
|---|---|---|---|---|---|---|---|
| Time (minutes) | HCl salt | MsOH salt | BsOH salt | 4-CBS salt | 4-EBS salt | 2,4-DMBS salt | 2,5-DMBS salt |
| 45 | 6.42 | 0.00 | 0.75 | 1.48 | 0.00 | 0.00 | 0.06 |
| 60 | 7.76 | 0.19 | 0.93 | 1.81 | 0.13 | 0.03 | 0.10 |
| 75 | 8.82 | 0.35 | 1.05 | 2.01 | 0.19 | 0.03 | 0.16 |
| 90 | 9.53 (sherbet state) | 0.35 | 1.08 | 2.14 | 0.22 | 0.06 | 0.19 |
| 120 | 9.89 | 0.42 | 1.23 | 2.30 | 0.41 | 0.06 | 0.26 |
| 150 | 10.39 | 0.39 | 1.02 | 2.17 | 0.54 | 0.06 | 0.32 |
| 180 | 10.69 | 0.55 | 1.08 | 2.27 | 0.36 | 0.06 | 0.32 |

Experimental Example 5

Comparison of Hygroscopicity

Figure 14:
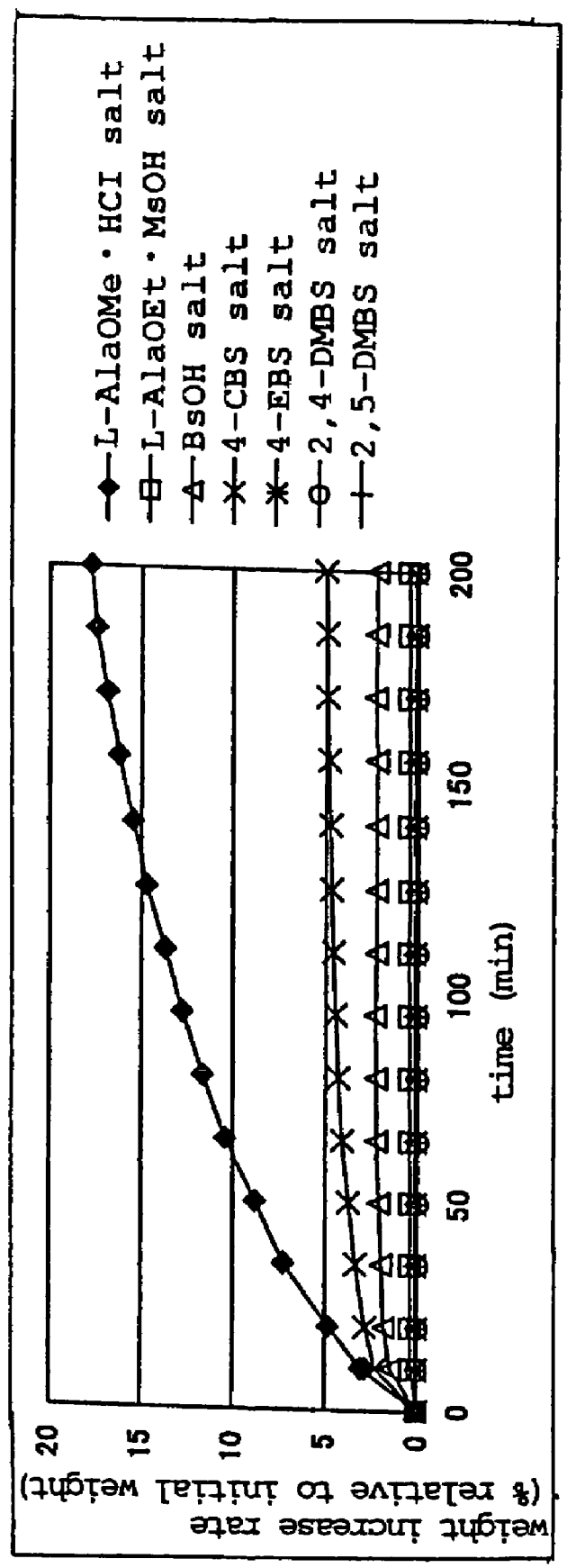
FIG. 14 is a graph of the results presented the values in Table 5.

The L-Ala-OMe HCl salt, L-Ala-OEt MsOH salt, L-Ala-OEt BsOH salt, L-Ala-OEt 4-CBS salt, L-Ala-OEt 4-EBS salt, L-Ala-OEt 2,4-DMBS salt, and L-Ala-OEt 2,5-DMBS salt were measured in an amount of about 0.3 g each, left standing in a thermostatic chamber at a temperature of 24 EC and a humidity of 60 to 66% RH, and the hygroscopicity was compared based on the weight gain with the lapse of time. A part of the crystal of the L-Ala-OMe HCl salt was liquefied in 35 minutes, and the liquefied increased thereafter with the lapse of time. After 125 minutes, the whole mass like a sherbet. In contrast, the other salts showed almost no change in weight with the lapse of time, and liquefaction was not observed. The results are shown in Table 5 FIG. 14.

Experimental Example 6

Corrosiveness Evaluation

A small amount of each of the L-Ala-OMe HCl salt, L-Ala-OEt HCl salt, L-Ala-OEt MsOH salt, L-Ala-OEt BsOH salt, L-Ala-OEt 4-CBS salt, L-Ala-OEt 4-EBS salt, L-Ala-OEt 2,4-DMBS salt, and L-Ala-OEt 2,5-DMBS salt was placed on a stainless plate (SUS 316 L), left standing in a thermostatic chamber at a temperature of 22 EC and a humidity of 30% RH, and the corrosion state of the stainless plate was observed. When one day passed, the L-Ala-OEt HCl salt developed a brown rust on the stainless plate. After 6 days, the L-Ala-OEt HCl salt developed more rust, and the L-Ala-OMe HCl salt developed a rust. After the lapse of 7 days, the plate was moved to the atmosphere at 24° C. and 65% RH. The rust expanded in 6 hours. The L-Ala-OEt MsOH salt was liquefied in its entirety, and the L-Ala-OEt BsOH salt and L-Ala-OEt 4-CBS salt were partly liquefied, though without rust. The other salts showed no change, and the stainless plate had no rust. The results are shown in Table 6.

TABLE 5

| | | | weight increase rate (%) | | | | |
|---|---|---|---|---|---|---|---|
| | L-Ala- | | | L-Ala-OEt | | | |
| Time (minutes) | OMe HCl salt | MsOH salt | BsOH salt | 4-CBS salt | 4-EBS salt | 2,4-DMBS salt | 2,5-DMBS salt |
| 0 | 0.00 | 0.00 | 0.00 | 0.00 | 0.00 | 0.00 | 0.00 |
| 10 | 3.03 | 0.32 | 1.46 | 2.26 | 0.09 | 0.00 | 0.00 |
| 20 | 4.85 | 0.35 | 1.80 | 2.83 | 0.09 | 0.00 | 0.03 |
| 35 | 7.30 (partly liquefied) | 0.38 | 1.97 | 3.38 | 0.15 | 0.00 | 0.03 |
| 50 | 8.84 | 0.38 | 2.11 | 3.77 | 0.15 | 0.00 | 0.09 |
| 65 | 10.42 | 0.41 | 2.22 | 4.10 | 0.15 | 0.00 | 0.06 |
| 80 | 11.65 | 0.44 | 2.25 | 4.31 | 0.15 | 0.03 | 0.06 |
| 95 | 12.77 | 0.44 | 2.28 | 4.46 | 0.15 | 0.00 | 0.06 |
| 110 | 13.69 | 0.48 | 2.22 | 4.58 | 0.18 | 0.03 | 0.12 |
| 125 | 14.74 (sherbet state) | 0.44 | 2.22 | 4.70 | 0.15 | 0.03 | 0.06 |
| 140 | 15.46 | 0.48 | 2.22 | 4.76 | 0.18 | 0.03 | 0.09 |
| 155 | 16.23 | 0.48 | 2.22 | 4.82 | 0.18 | 0.03 | 0.09 |
| 170 | 16.88 | 0.51 | 2.28 | 4.94 | 0.18 | 0.06 | 0.09 |
| 185 | 17.43 | 0.48 | 2.25 | 4.94 | 0.15 | 0.06 | 0.09 |
| 200 | 17.77 | 0.51 | 2.25 | 5.03 | 0.21 | 0.06 | 0.12 |

TABLE 6

Evaluation of corrosiveness

| | | Days lapsed | | |
|---|---|---|---|---|
| | 1 day later | 6 days later | 7 days later | 8 days later (24° C., 65% RH) |
| L-Ala-OMe HCl salt | No change | Development of rust on a part of stainless plate | No change from 6 days later | Expansion of rust on stainless plate (entire sherbet) |
| L-Ala-OEt HCl salt | Development of rust on a part of stainless plate (partly liquefied) | Expansion of rust on stainless plate (entirely liquefied) | No change from 6 days later | Expansion of rust on stainless plate (entirely liquefied) |
| MsOH salt | No change | No change | No change | No rust (entirely liquefied) |
| BsOH salt | No change | No change | No change | No rust (partly liquefied) |
| 4-CBS salt | No change | No change | No change | No rust (partly liquefied) |
| 4-EBS salt | No change | No change | No change | No change |
| 2,4-DMBS salt | No change | No change | No change | No change |
| 2,5-DMBS salt | No change | No change | No change | No change |

Experimental Example 7

Evaluation of Hygroscopicity

Figure 15:
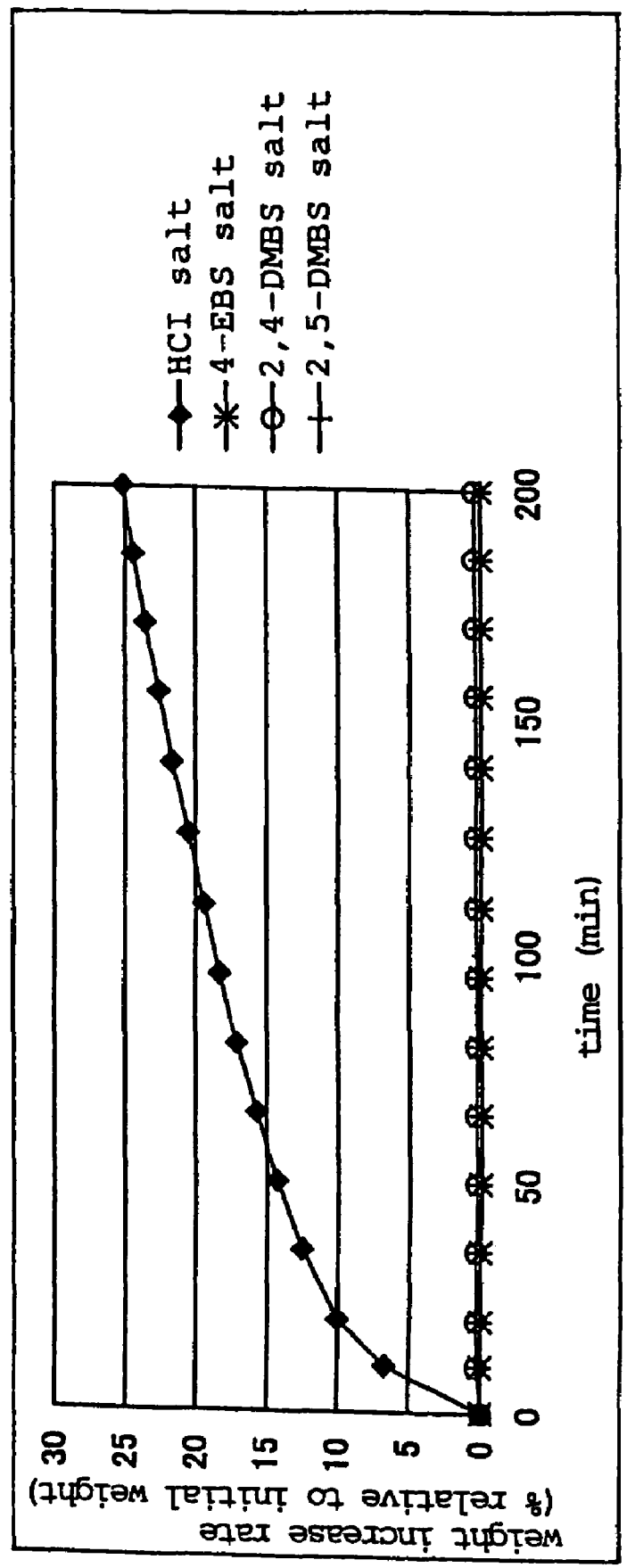
FIG. 15 is a graph of the results presented the values in Table 7.

The L-Ala-OMe HCl salt, L-Ala-OMe 4-EBS salt, L-Ala-OMe 2,4-DMBS salt, and L-Ala-OMe 2,5-DMBS salt were measured in an amount of about 0.3 g each, left standing in a thermostatic chamber at temperature of 24 EC and a humidity of 60 to 66% RH, and the hygroscopicity was compared based on the weight gain with the lapse of time. A part of the crystal of the L-Ala-OMe HCl salt was liquefied in 10 minutes, and the entirety became a sherbet in 20 minute. The liquefied portion increased thereafter with the lapse of time. After 80 minutes, the whole was liquefied. In contrast, the other salts showed almost no change in weight with the lapse of time, and liquefaction was not observed. The results are shown in Table 7 and FIG. 15.

TABLE 7

| Time | weight increase rate (%) L-Ala-OMe | | | |
|---|---|---|---|---|
| (min) | HCl salt | 4-EBS salt | 2,4-DMBS salt | 2,5-DMBS salt |
| 0 | 0.00 | 0.00 | 0.00 | 0.00 |
| 10 | 6.74 (partly liquefied) | 0.06 | 0.33 | 0.06 |
| 20 | 10.06 (sherbet state) | 0.06 | 0.37 | 0.06 |
| 35 | 12.52 | 0.06 | 0.37 | 0.06 |
| 50 | 14.31 | 0.06 | 0.37 | 0.03 |
| 65 | 15.69 | 0.03 | 0.37 | 0.03 |
| 80 | 17.16 (entirely liquefied) | 0.06 | 0.37 | 0.03 |
| 95 | 18.31 | 0.06 | 0.37 | 0.00 |
| 110 | 19.42 | 0.03 | 0.40 | 0.03 |
| 125 | 20.54 | 0.06 | 0.43 | 0.06 |
| 140 | 21.66 | 0.06 | 0.40 | 0.00 |
| 155 | 22.62 | 0.06 | 0.43 | 0.00 |

TABLE 7-continued

| Time | weight increase rate (%) L-Ala-OMe | | | |
|---|---|---|---|---|
| (min) | HCl salt | 4-EBS salt | 2,4-DMBS salt | 2,5-DMBS salt |
| 170 | 23.55 | 0.06 | 0.47 | 0.03 |
| 185 | 24.41 | 0.06 | 0.50 | 0.03 |
| 200 | 25.14 | 0.06 | 0.50 | 0.06 |

Industrial Applicability

Crystals of alanine alkyl ester sulfonates, which are useful as intermediates for the production of pharmaceutical compounds which having an alanine skeleton or as an alanine-containing peptide synthetic reagent, and which exhibit low hygroscopicity and low corrosiveness, can be obtained by the method of the present invention. The sulfonic acid to be used in the present invention can be either obtained industrially economically or can be easily produced. In addition, the alanine alkyl ester sulfonates of the present invention can be easily produced industrially.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A crystal of an alanine alkyl ester sulfonate, which is represented by formula (1):

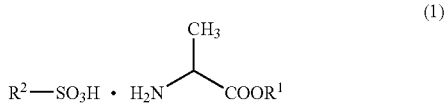

wherein R¹ is a methyl group or an ethyl group, provided that when R¹ is a methyl group, R² is an ethylphenyl group or a dimethylphenyl group; and when R¹ is an ethyl group, R² is a methyl group, a phenyl group, a chlorophenyl group, an ethylphenyl group, or a dimethylphenyl group.

2. The crystal of claim 1, wherein, when R¹ is a methyl group, R² is a 4-ethylphenyl group, a 2,4-dimethylphenyl group, or a 2,5-dimethylphenyl group; and when R¹ is an ethyl group, R² is a methyl group, a phenyl group, a 4-chlorophenyl group, a 4-ethylphenyl group, a 2,4-dimethylphenyl group, or a 2,5-dimethylphenyl group.

3. The crystal of claim 1, wherein R¹ is an ethyl group.

4. The crystal of claim 1, wherein R¹ is a methyl group.

5. The crystal of claim 1, wherein said alanine alkyl ester is an L form.

6. The crystal of claim 1, which is a crystal of an alanine alkyl ester methanesulfonate.

7. The crystal of claim 1, which is a crystal of L or D-alanine alkyl ester methanesulfonate.

8. A crystal, selected from the group consisting of:
a crystal of L-alanine ethyl ester methanesulfonate;
a crystal of L-alanine ethyl ester benzenesulfonate;
a crystal of L-alanine ethyl ester 4-chlorobenzenesulfonate;
a crystal of L-alanine ethyl ester 4-ethylbenzenesulfonate;
a crystal of L-alanine ethyl ester 2,4-dimethylbenzenesulfonate;
a crystal of L-alanine ethyl ester 2,5-dimethylbenzenesulfonate;
a crystal of L-alanine methyl ester 4-ethylbenzenesulfonate;
a crystal of L-alanine methyl ester 2,4-dimethylbenzenesulfonate and
a crystal of L-alanine methyl ester 2,5-dimethylbenzenesulfonate.

9. The crystal according to claim 8, which is a crystal of L-alanine ethyl ester methanesulfonate.

10. The crystal according to claim 8, which is a crystal of L-alanine ethyl ester benzenesulfonate.

11. The crystal according to claim 8, which is a crystal of L-alanine ethyl ester 4-chlorobenzenesulfonate.

12. The crystal according to claim 8, which is a crystal of L-alanine ethyl ester 4-ethylbenzenesulfonate.

13. The crystal according to claim 8, which is a crystal of L-alanine ethyl ester 2,4-dimethylbenzenesulfonate.

14. The crystal according to claim 8, which is a crystal of L-alanine ethyl ester 2,5-dimethylbenzenesulfonate.

15. The crystal according to claim 8, which is a crystal of L-alanine methyl ester 4-ethylbenzenesulfonate.

16. The crystal according to claim 8, which is a crystal of L-alanine methyl ester 2,4-dimethylbenzenesulfonate.

17. The crystal according to claim 8, which is a crystal of L-alanine methyl ester 2,5-dimethylbenzenesulfonate.

18. A method of preparing a crystal of an alanine alkyl ester sulfonate represented by formula (1):

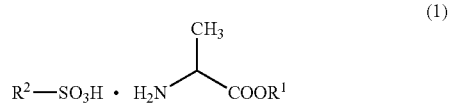

wherein R¹ is a methyl group or an ethyl group, provided that when R¹ is a methyl group, R² is an ethylphenyl group or a dimethylphenyl group; and when R¹ is an ethyl group, R² is a methyl group, a phenyl group, a chlorophenyl group, an ethylphenyl group, or a dimethylphenyl group, wherein said method comprises:
(a) contacting an alanine alkyl ester represented by formula (2):

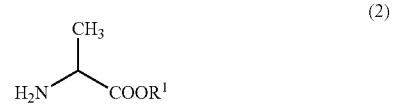

wherein R¹ is a methyl group or an ethyl group, with a sulfonic acid, to obtain an alanine alkyl ester sulfonate; and
(b) crystallizing said alanine alkyl ester sulfonate.

19. The method of claim 18, wherein, when R¹ is a methyl group, R² is a 4-ethylphenyl group, a 2,4-dimethylphenyl group, or a 2,5-dimethylphenyl group; and when R¹ is an ethyl group, R² is a methyl group, a phenyl group, a 4-chlorophenyl group, a 4-ethylphenyl group, a 2,4-dimethylphenyl group, or a 2,5-dimethylphenyl group.

20. The method of claim 18, wherein R¹ is an ethyl group and R² is a methyl group.

* * * * *